(12) United States Patent
Te'eni

(10) Patent No.: US 6,227,039 B1
(45) Date of Patent: May 8, 2001

(54) SYSTEM AND METHOD FOR CONTROLLING CONCRETE PRODUCTION

(76) Inventor: Moshe Te'eni, 53 Ir Shemesh Street, Tel Aviv 69806 (IL)

( * ) Notice: Subject to any disclaimer, the term of this patent is extended or adjusted under 35 U.S.C. 154(b) by 0 days.

(21) Appl. No.: 09/303,565

(22) Filed: May 3, 1999

Related U.S. Application Data

(63) Continuation of application No. 08/981,807, filed on Jan. 6, 1998, now Pat. No. 5,948,970.

(30) Foreign Application Priority Data

Jul. 6, 1998 (IL) ........................................................ 114494

(51) Int. Cl.[7] ............................ G01N 11/00; G01N 11/14; C08L 95/00; C04B 7/36
(52) U.S. Cl. ........................ 73/54.03; 73/54.03; 73/53.04
(58) Field of Search ................................. 73/54.03, 53.04, 73/54.23, 54.37, 54.39

(56) References Cited

U.S. PATENT DOCUMENTS

| | | | | |
|---|---|---|---|---|
| 1,960,226 | * | 5/1934 | Schoenberg | 265/11 |
| 2,247,553 | * | 7/1941 | Hutchinson | 73/51 |
| 3,269,171 | * | 8/1966 | Bruss et al. | 73/60 |
| 3,640,121 | * | 2/1972 | Mercier | 73/54 |
| 3,640,126 | | 2/1972 | Te'eni | 73/88 |
| 3,974,679 | | 8/1976 | Nasser | 73/15.6 |
| 4,210,015 | * | 7/1980 | Euzen et al. | 73/61.1 R |
| 4,332,158 | * | 6/1982 | Osborne | 73/59 |
| 4,343,190 | * | 8/1982 | Danko et al. | 73/846 |
| 4,383,864 | | 5/1983 | Trujillo et al. | 281/106 |
| 4,464,928 | * | 8/1984 | Dealy | 73/54 |
| 4,534,210 | * | 8/1985 | Reeves | 73/59 |
| 4,571,989 | * | 2/1986 | Dealy | 73/60 |
| 4,602,501 | * | 7/1986 | Hirata | 73/54 |
| 4,789,244 | | 12/1988 | Dunton et al. | 366/12 |
| 4,825,700 | | 5/1989 | Vardoulakis et al. | 73/749 |
| 4,900,154 | | 2/1990 | Waitzinger et al. | 366/366 |
| 4,930,346 | | 6/1990 | Paakkinen et al. | 73/59 |
| 4,941,346 | | 7/1990 | Suzuki et al. | 73/54 |
| 5,131,265 | * | 7/1992 | Tobin et al. | 63/54.23 |
| 5,160,540 | | 11/1992 | Johansson et al. | 106/672 |
| 5,258,622 | | 11/1993 | Pratt, Jr. | 250/390.05 |
| 5,303,578 | * | 4/1994 | Williams et al. | 73/54.24 |
| 5,321,974 | | 6/1994 | Hemmings et al. | 73/54.31 |
| 5,527,387 | | 6/1996 | Anderson | 693/106 |
| 5,877,410 | * | 3/1999 | Duke | 73/54.28 |

FOREIGN PATENT DOCUMENTS 0 126 573   5/1984   (EP).

OTHER PUBLICATIONS

Rheology of Fresh High–Performance Concrete; Chong Hu, Franciois de Larrard; Cement and Concrete Research v 26 n 2 Feb. 1996 pp 283–294.

* cited by examiner

Primary Examiner—Hezron Williams
Assistant Examiner—J. David Wiggins
(74) Attorney, Agent, or Firm—Foley & Lardner

(57) ABSTRACT

A measuring system for measuring rheological properties of a concrete mix tested when contained, the system comprising, a surface in contact with part of a mass of said concrete mix; a shearing unit for effecting shear deformation in said mass, along the direction of a shearing plane crossing through said concrete mass; and at least one sensor which senses a measure of the force which is transferred to said surface by said concrete mass as a result of said shear deformation under at least two measurement environments defining at least two different stress states, where said two measurement environments are created by said shearing unit effecting a shear deformation and where said two different measurement environments are characterized by having substantially different forces perpendicular to the shear plane of said shear deformation.

31 Claims, 16 Drawing Sheets

SYSTEM AND METHOD FOR CONTROLLING CONCRETE PRODUCTION

This patent application is a continuation of application Ser. No. 08/981,807, which is now U.S. Pat. No. 5,948,970 dated Sep. 7, 1999.

FIELD OF THE INVENTION

The present invention relates to concrete in general and more particularly to an improved system and method for the design and control of concrete production.

BACKGROUND OF THE INVENTION

Concrete is generally prepared according to a mix design which specifies the proportions of the various material constituents used to produce the concrete. For example, a concrete mix commonly described as a "1:2:4" mix refers to mix proportions of one part of cement to 2 parts of fine aggregate (such as sand) to 4 parts of coarse aggregate (such as gravel). The proportion between cement and water is also usually specified. The design of the mix may depend on many factors and specific engineering requirements.

Some of these requirements relate to the rheological properties required from the mix in its fresh state during its transportation, placement and compaction. The requirements are determined to suit specific conditions of application, for example use of pumping in transportation, the measure of vibration employed during compaction, the measure of cohesion and mobility needed during placing, etc.

Whilst the mechanical properties of hardened concrete are mainly influenced by the water/cement ratio of the mix, the rheological properties of the fresh mix are strongly influenced by the water content and also strongly by the particle size distribution of the solid particles in the mix and by the relative content of fine particles, in the aggregate system.

The particle size distribution in the mix depends on the mix design as well as on the particle size distribution within each of the constituents from which the mix is produced. A change in the character or size distribution of one of the aggregate constituents of a mix having a given design, results in changes in its rheological properties.

To offset such changes, the mix design can be modified. Such modifications are commonly conducted under the supervision of a concrete technician. The suitability of the mix in its fresh state to a given application requirements is commonly measured through the shear deformation of the mix. This is commonly determined by measuring "workability" vis a known test method. A common test method, known as the "Slump Test", is especially suited for the measurement of the workability of mixes having a soft consistency. A supporting frame in which a mass of concrete has been cast is lifted, allowing the concrete body to freely slump under gravity. The drop in height of the concrete mass is measured.

A test method commonly used for the definition of the "workability" of dry mixes measures the time, in seconds, it takes a body of concrete to change its shape from a truncated cone to a cylindrical shaped body under the effect of standard vibration.

Adjustments in workability are commonly achieved during production of concrete mixes by changing the quantity of water in the mix.

Also common in the monitoring of workability of a concrete mix whilst in a mixing drum is the measurement of the force required to mix the concrete by rotation of the drum or the paddles in the drum. A measurement of the force can be obtained by monitoring the hydraulic pressure or current needed to operate the mixer motor.

The resistance to deformation of a mix can be regulated by changing the amount of water added to it. It is known how to effect an automatic adjustment to the amount of water in the mix so that a constant workability is maintained. For example, European Patent Publication 0 126 573 A1 to Durant proposed a method of controlling the quality of the concrete mix in mobile mixers by measuring the workability of the concrete mix and selectively adding water to achieve the required consistency for the concrete mix.

Different concrete mixes can exhibit equal workabilities when measured by different techniques and yet can possess totally different rheological properties relating to their suitability for commonly required applications. For example, when a concrete mix is designed, for pumping, its rheology is especially adjusted to be pumpable under the set of conditions.

A standard mix design "assumes" that the characteristics of the various constituents are constant. However, in practice, the characteristics of a specific aggregate may vary in time. It may become necessary to change the mix proportions in order to maintain the desired mix characteristics. Unfortunately, present technology does not have any objective procedure of accurately defining the rheological requirements and methodically making changes to the mix proportions so as to ensure that the final product has the required characteristics. The changes, when made, are according to a subjective and qualitative assessment of a concrete technician. It is known to alter the amount of water within a concrete mix in order to change the workability of the mix.

SUMMARY OF THE INVENTION

Commonly used workability tests for concrete are conventions chosen to generate deformation in a concrete mix under set conditions for the purpose of providing a measure of the resistance of the concrete mix to deformation. Applicant has recognized that the resistance to deformation of a concrete mix is influenced by the stress state acting on the shear planes during the deformation. Furthermore, Applicant has realized that different mixes are differently affected in terms of their resistance to deformation following a change in the stress states acting on the shear planes in a deformational regime.

Since, in reality, concrete is applied under various deformational modes and regimes producing different stress states, it is important to provide a parameter which measures the change in the resistance to deformation of a given mix under changing stress states. Such a parameter reflects the internal friction of the mix governing its behavior between the liquid and rigid aggregate phases.

The provision of such a characteristic in the definition of the behavior of concrete provides an important addition to the presently available definition of resistance to deformation which is restricted to a particular workability test method conducted under a given deformational mode. A vector consisting of at least two such variables is hereinafter called the "Rheological Profile" of the mix. In order to obtain readings of two such variables, at least two measurements of resistance to deformation, or related values, are conducted under at least two "measurement environments". A measurement environment is a domain within a concrete mass having a characteristic stress configuration (state and level) under a given condition in a deformational mode in the concrete mass.

Two measurement environments could be provided, for example, by taking measurements under at least two deformational regimes under changing stress states. The invention offers methods by which a concrete mix undergoes shear in a sequence of at least two changing deformational modes during which the resistance to deformation or related values, are measured.

In this way, a scale is formed by which it is possible to measure and define variables of the rheological profile of a mix. By testing a sequence of a few mixes having controlled changes in the mix design, the mix required to produce any particular rheological profile is established.

There is therefore provided, in accordance with a preferred embodiment of the present invention, a measuring system which includes a surface, a shearing unit and at least one sensor. The surface is in contact with a part of a mass of the concrete mix. The shearing unit effects shear deformation in the mass. The sensor senses a measure of the force which is transferred to the surface by the concrete mass as a result of the shear deformation.

Additionally, in accordance with a preferred embodiment of the present invention, the surface is part of a confining envelope and the sensor is mounted on the confining envelope. There can be two sensors located on two different places of the confining envelope. Alternatively, the two sensors can be located in two different measurement environments along the confirming envelope.

Alternatively, in accordance with a further preferred embodiment of the present invention, the shearing unit is a rigid body and the surface is a contact surface of the rigid body in contact with the mass of concrete. In this embodiment, the sensor measures the resistance of the shearing unit to movement present when producing the shear deformation. Furthermore, there is a space defined between the confining envelope and the contact surface which changes shape with the movement of the rigid body during shear deformation. The sensor measures the change in resistance following the change in shape of the space.

Moreover, in accordance with both preferred embodiments of the present invention, the measuring system includes a vibrator. The two different measurement environments are: operating with only the shear deformation unit and operating with both the shear deformation unit and the vibrator. The sensors can be located at two different distances from the vibrator.

Further, in accordance with a preferred embodiment of the present invention, the shearing unit is any one or a combination of the following means: a mechanical mixer, a paddle mixer, a mechanical screw, a plunger, a hydraulic pump, a propeller and a rotatable drum. The confining envelope is any one or a combination of the following container: a pipe, a box, a drum and a block forming frame.

More specifically, in accordance with a still further preferred embodiment of the present invention, there is provided apparatus for measuring the rheological profile of concrete within a container. The apparatus includes a) a U-shaped shear box having openings at two ends, b) an upstand, c) a piston for pushing the U-shaped shear box within the concrete towards and over the upstand, thereby to force the concrete out the openings and either d) stress sensors placed on two non-parallel planes for measuring the stress in the planes as a function of the shear induced in the concrete by the shear inducing apparatus or e) movement sensors for sensing the movement of the piston. The apparatus can also include a vibrator and/or at least one acceleration sensor attached to the shear box. The apparatus can also include connecting rods between the shear box and a frame onto which are mounted stress sensors and/or pressure sensors for sensing the pressure pushing the piston.

There is also provided, in accordance with a still further preferred embodiment of the present invention, a method for generating the rheological profile of a concrete mix. The steps of the method are:

a. sensing at least one measure of the force which is transferred to a surface in contact with a part of a mass of the concrete mix under at least two different shear deformation modes;

b. from the output of step (a), determining a) the sensitivity of each of the at least one measure to a change in deformation mode and b) the workability of the mix; and c. creating the rheological profile from at least the sensitivity and the workability.

Moreover, in accordance with this preferred embodiment of the present invention, the shear deformation is conducted once while the mass is under vibration and once while the mass is not under vibration. The measure of the force can be any of the following variables: movement, shear rate, acceleration, pressure and force.

There is additionally provided, in accordance with a still further preferred embodiment of the present invention, a method for dynamically designing concrete to have desired rheological properties. The method includes the steps of:

a. preparing a concrete mix in a concrete plant in accordance with a mix design indicating the proportions of solid and water components of the concrete;

b. testing the prepared concrete mix with a concrete tester;

c. generating a rheological profile of the concrete mix from output of the step of testing;

d. comparing the generated rheological profile with a desired rheological profile defining desired properties of the concrete to be produced by the plant; and e. adjusting the solid components of the mix design in order to produce concrete having a rheological profile which is compatible with the desired rheological profile.

Moreover, in accordance with this preferred embodiment of the present invention, the steps of preparing, testing and generating are repeated for at least three concrete mixes at least two of which have different proportions of solid components and at least two of which have different water to solid ratios.

Still further, in accordance with this preferred embodiment of the present invention, the rheological profiles include a measure of workability and at least one of the following factors: expressions or functions related to the: stress state sensitivity, stress distribution, shear rate sensitivity, vibration decay, vibratability, pumpability and deformability. The rheological properties can each have a range of allowable values.

There is also provided, in accordance with a still further preferred embodiment of the present invention, a system which designs concrete to have desired rheological properties. The system includes a plant, a concrete profile measuring unit and a mix changing unit. The plant prepares a concrete mix in accordance with a mix design indicating the proportions of the solid components and water of the concrete. The concrete profile measuring unit, such as those described hereinabove, measures a rheological profile of the concrete produced by the plant. The mix changing unit receives the measured rheological profile and a desired rheological profile defining desired properties of the concrete produced by the plant and indicates to the plant to adjust the solid components of the concrete mix, as many times as necessary, in order to produce concrete which has a rheological profile which is compatible with the desired rheological profile.

Moreover, in accordance with this preferred embodiment of the present invention, the mix changing unit includes a search unit which receives a quality of change criterion and determines the mix design change which will provide concrete having a rheological profile which is compatible with the desired rheological profile and which fits within the quality of change criterion. The criterion can be a function of the cost of the mix. The concrete profile measuring unit can be located within or away from the plant.

BRIEF DESCRIPTION OF THE DRAWINGS

These and further construction features of the invention will be better appreciated in the light of the ensuing description of a preferred embodiment thereof, given by way of example only with reference to the accompanying drawings wherein.

DETAILED DESCRIPTION OF PREFERRED EMBODIMENTS

Figure 1:
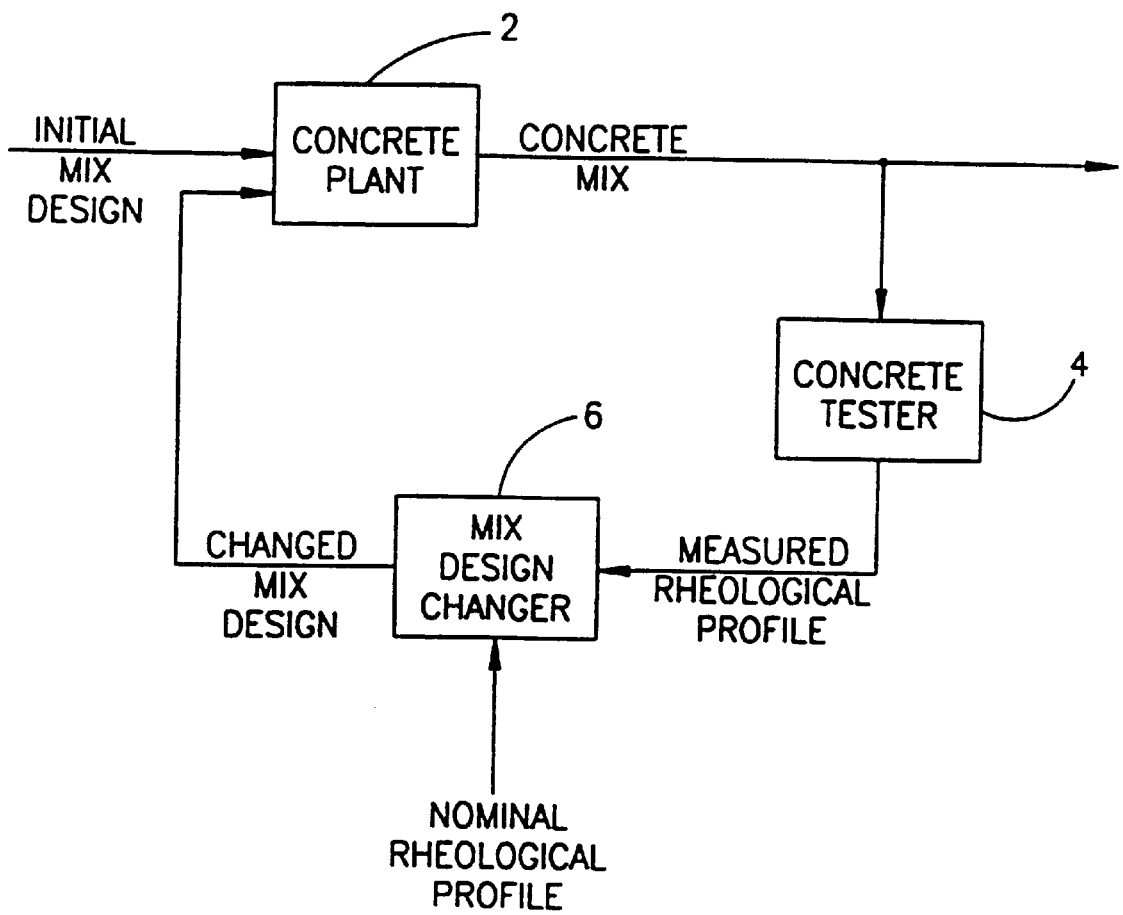
FIG. 1 is a block diagram illustration of a system for controlling concrete production in accordance with a preferred embodiment of the present invention.

Reference is now made to FIG. 1 which illustrates a system for controlling concrete production, constructed and operative in accordance with a preferred embodiment of the present invention. The system comprises a concrete plant 2, a concrete tester 4 and a mix design changer 6.

The concrete plant 2 can be any electronically controlled prior art concrete batching plant which produces concrete from a mix design defining the ratios of fine sand, aggregate, water and cement from which to produce a desired concrete.

The concrete tester 4, described in more detail hereinbelow with respect to FIGS. 2, 3, 9–16, measures various properties of the concrete mix undergoing shear deformation. From these properties, a "rheological profile" can be produced (either in the concrete tester 4 or in the mix design changer 6) which will be described in more detail hereinbelow. The rheological profile defines the rheological nature of the concrete mix.

Figure 5:
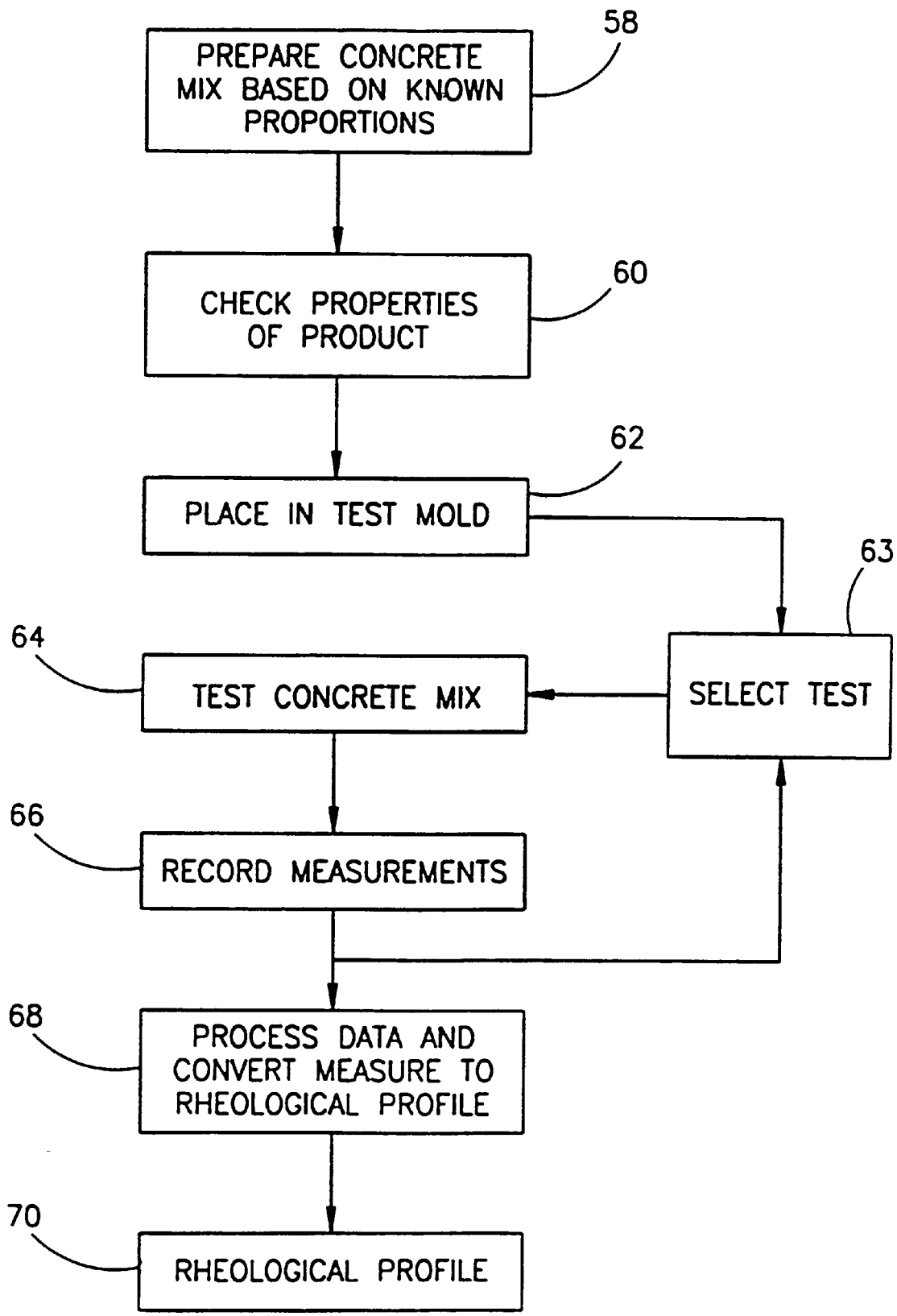
FIG. 5 is a flow chart illustration of the design of a nominal rheological mix.
Figure 6:
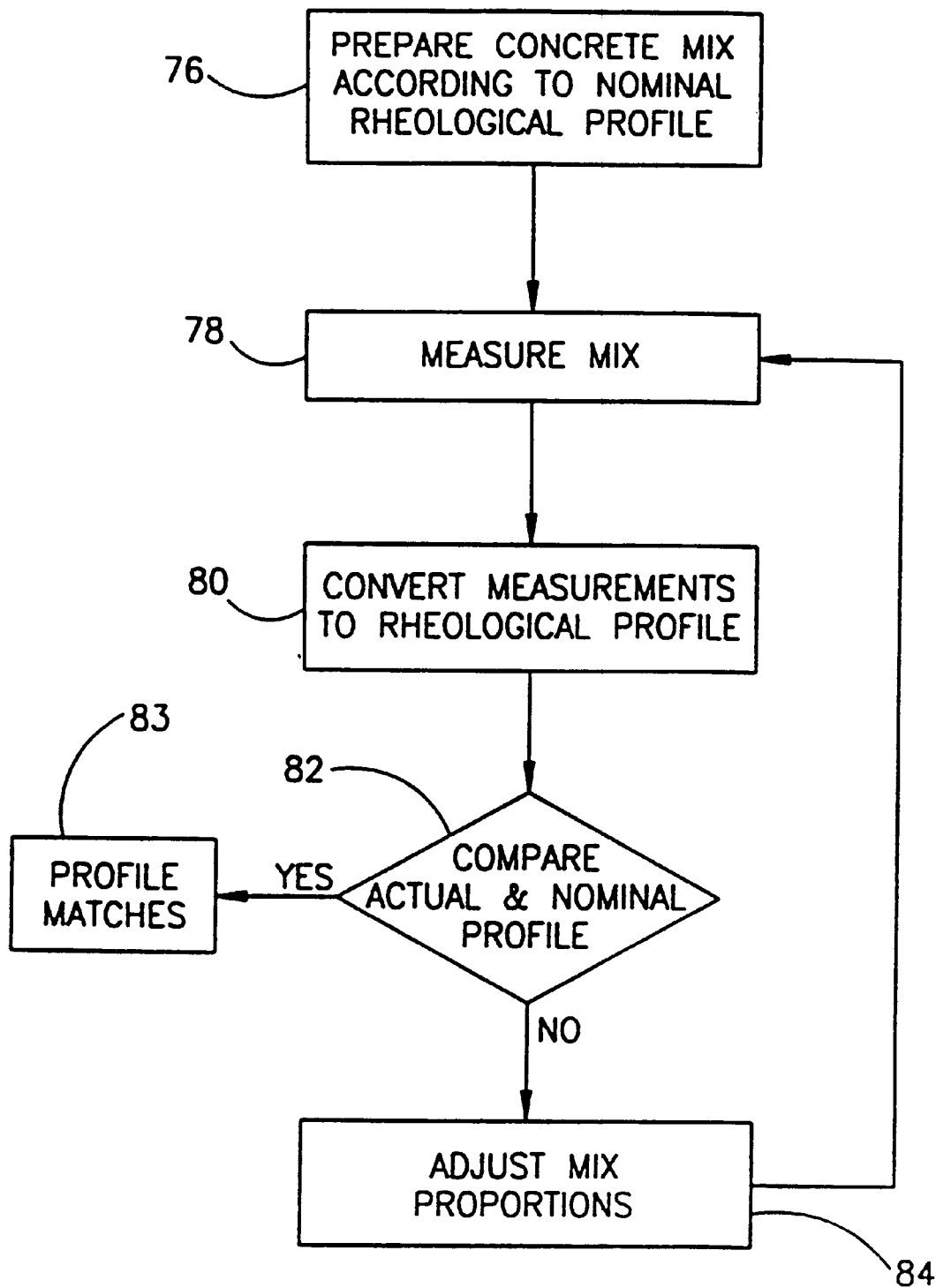
FIG. 6 is a flow chart illustration of the use of a nominal rheological profile to control a concrete mix being produced.

The mix design changer 6, described in more detail hereinbelow with respect to FIGS. 5 and 6, compares the measured rheological profile with a nominal rheological profile defined as required for the concrete to be produced. If the two match sufficiently closely, then the concrete which has been produced has the desired qualities. However, if the differences between the two rheological profiles exceed pre-defined limits, then the mix design changer 6 adjusts the percentages of fines to coarse aggregates, and/or water and cement contents, so that the concrete produced has the desired qualities.

In another situation in which there is no definition of a required rheological profile and where the concrete is being processed in a concrete processing device that induces shear deformation in the concrete mass, the operation of the plant (as opposed to the properties of the mass) can be monitored in a manner discussed hereinbelow to provide the data for the adjustments in the mix design. The resultant design of the concrete will be compatible with the requirements of the process parameters whilst also being compatible with a cost optimization criterion.

FIGS. 2, 3, 9–13 illustrate various measuring systems for generating the physical measurements which are the basis of the rheological profile. FIGS. 12–16 illustrate measuring units in conjunction with concrete manufacture, production, and transportation systems. For all systems, the concrete mass is mechanically disturbed to undergo a deformation under a given loading regime.

A First Concrete Tester

Figure 2:
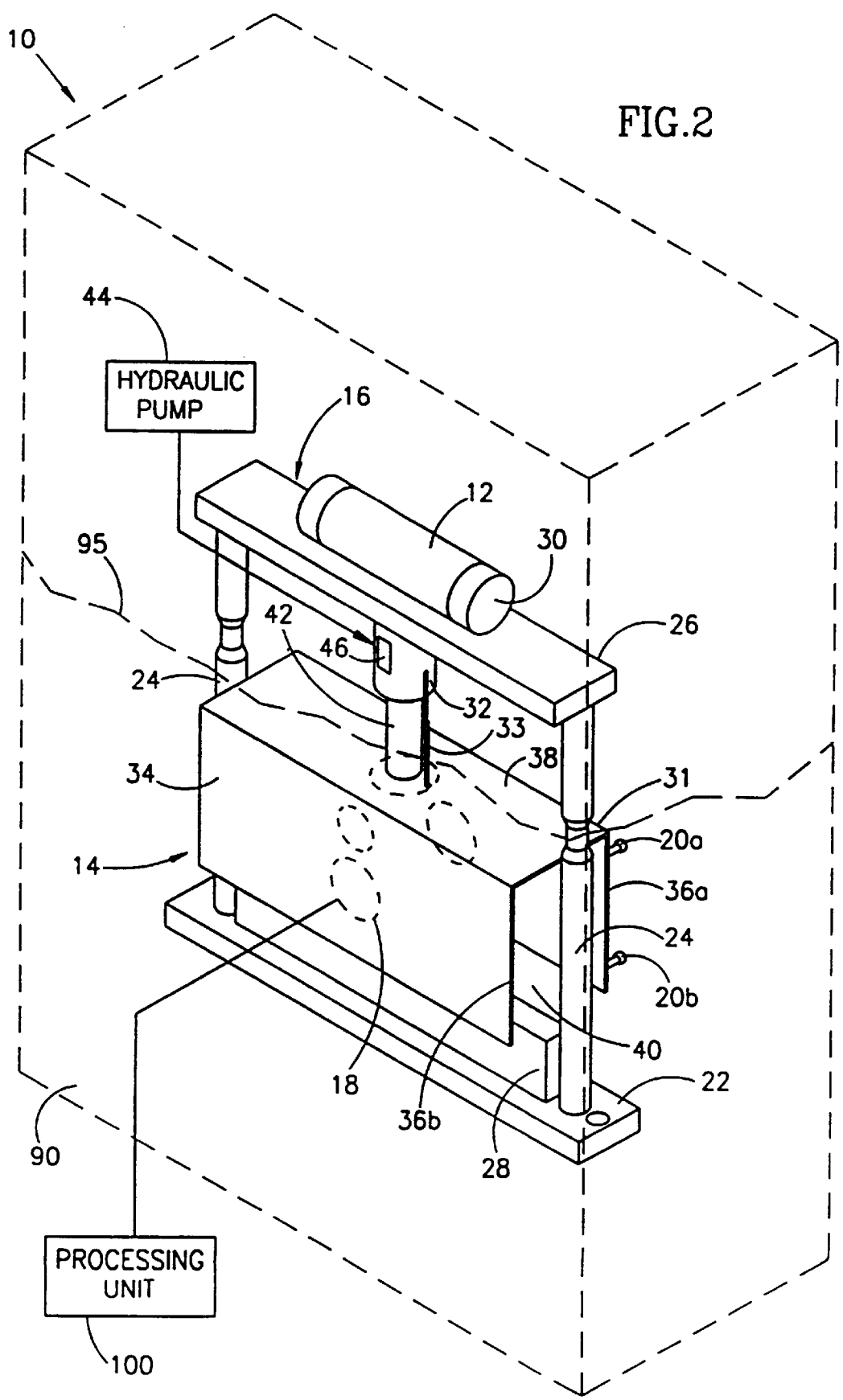
FIG. 2 is an isometric illustration of a device for testing concrete in accordance with a preferred embodiment of the present invention.

Reference is now made to FIG. 2 which illustrates a device for testing concrete, constructed and operative in accordance with a first embodiment of the invention.

The concrete testing device, generally designated 10, comprises vibrating apparatus 12 and shear inducing apparatus, generally designated 14, for determining the rheological characteristics of the concrete. Vibrating apparatus 12 shear inducing apparatus 14 are mounted on to a rigid frame, generally designated 16. A plurality of stress sensors 18 and acceleration sensors 20, of types known in the art, are attached to shear inducing apparatus 14. Other sensors, labeled 31, 33 and 46 sense a measure of other steering action.

Different concrete properties can be ascertained by placing the concrete testing device inside a container 90 of concrete, and for example, by subjecting the concrete to shear deforming and/or vibrating (as will be described in detail hereinbelow), and noting the readings of sensors 18 and 46. Sensors 18, 20, 31, 33 and 46 are connected, via a data acquisition system (not shown), to a processing unit 100 for processing the sensor data. The level of concrete for testing is indicated by line 95 and generally needs to cover the top of shearing apparatus 14.

Rigid frame 16 comprises a base portion 22, a pair of vertical members 24 and a top portion 26. An upstand 28 is mounted onto base portion 22 between vertical members 24.

Vibrating apparatus 12 comprises an electrical or pneumatic vibrator 30, of a type known in the art, mounted onto the upper side of top portion 26. Vibration induced by vibrator 30 is transferred via vertical members 24 to base portion 22 and upstand 28.

Sensors 20 comprise a pair of upper and lower acceleration sensors 20a and 20b, respectively, on the rigid frame 16. The difference in the readings from acceleration sensors 20a and 20b indicates the ability of the concrete to absorb vibration energy, from which a vibration decay factor can be determined. A tension sensor 31 is fitted to one of vertical members 24 to monitor the changing tension within the frame 16.

Shear inducing apparatus 14 includes a piston 32 and an inverted "U"-shaped shear box 34. Shear box 34 comprises two side panels 36a and 36b connected to a base panel 38 such that ends 40 are open. Piston 32 is fixed to top portion 26 and includes a piston rod 42 attached to base panel 38 of shear box 34. Piston 32 is attached to a power source 44, such as a hydraulic pump with a controllable rate. A pressure sensor 46 is fitted to piston 32 to measure the hydraulic pressure within piston 32. An electronic ruler 33 measures the extension of piston 32.

The plurality of stress sensors 18, shown by dashed circles, are attached to the inner face of side panels 36a and 36b and base panel 38 of shear apparatus 14.

Figure 3:
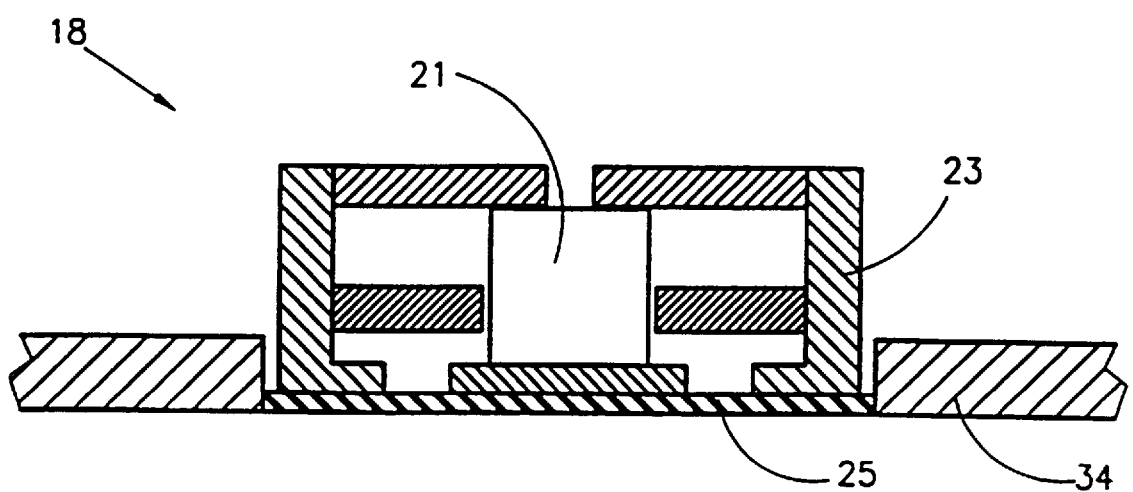
FIG. 3 is a side view illustration of a sensing device.

Reference is now briefly made to FIG. 3 which illustrates an exemplary sensor 18. The sensor comprises a pressure sensor 21, a housing 23 within which the pressure sensor 21 sits, and an elastomeric membrane 25 which is in contact with the concrete mass (indicated by dots). The membrane 25 is typically placed within the walls of the shear box 34 and defines the surface over which the pressure is measured.

Figure 4A:
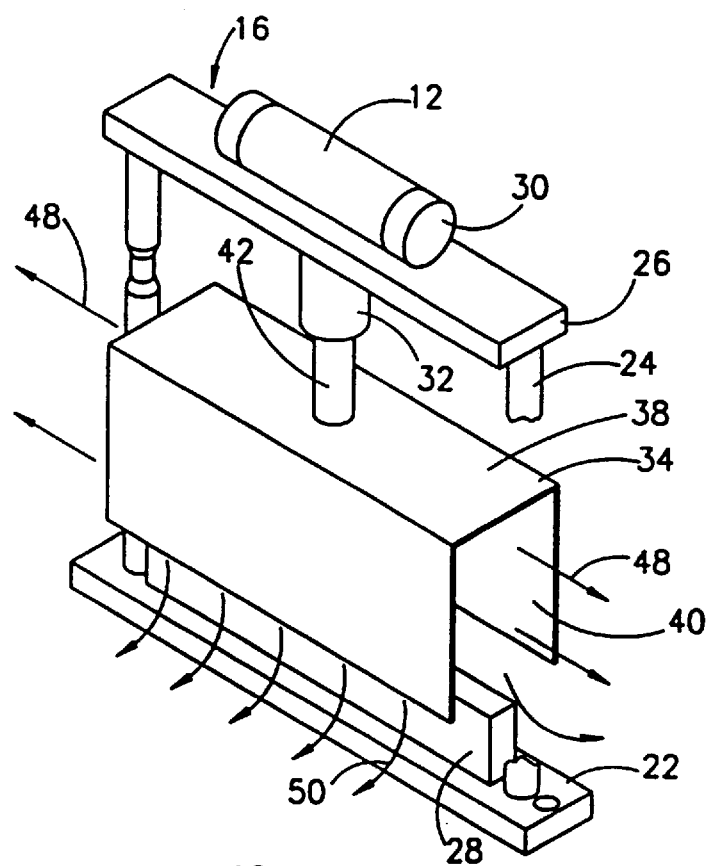
FIGS. 4A and 4B illustrate the operation of the device of FIG. 2.
Figure 4B:
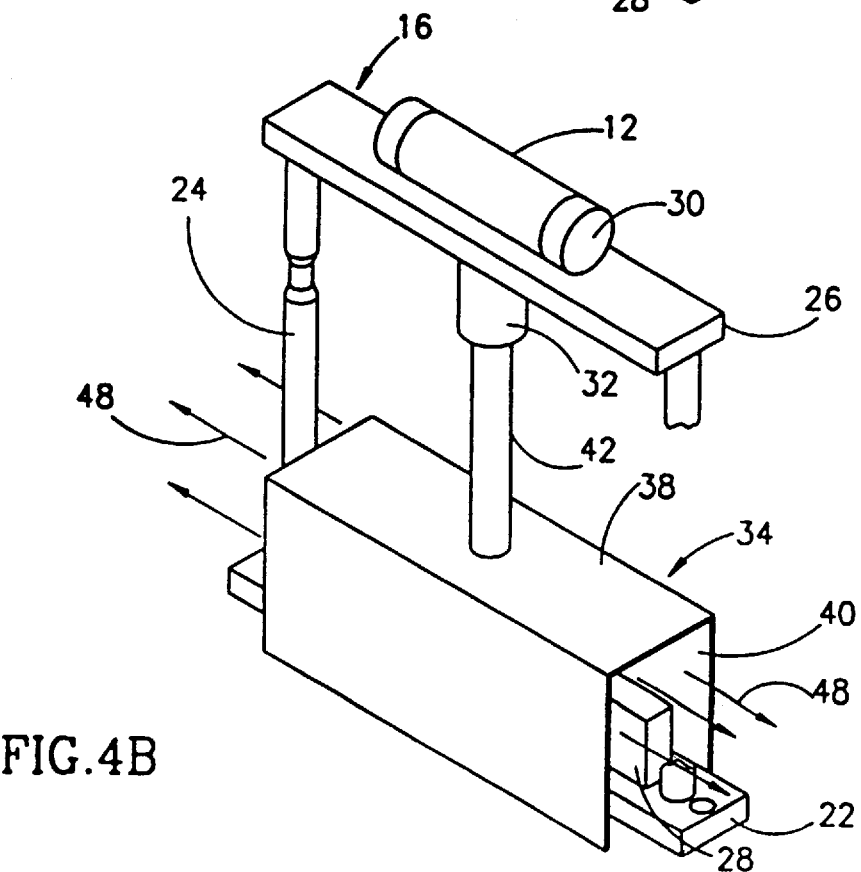

Reference is now also made to FIGS. 4A and 4B which show the operation of shear box 34. FIG. 3A shows piston rod 42 and shear box 34 in an intermediate position. FIG. 3B shows piston rod 42 extended to its maximum position.

Extending piston 42 pushes shear box 34 downwards at a controlled rate and forces the concrete sideways (shown by arrows 48) out of the open ends 40 of shear box 34 downwards (shown by arrows 50) over upstand 28. The width of base panel 38 is greater than the width of base portion 22. Thus, as piston rod 42 is extended and shear box 34 correspondingly descends downwards, side panels 36a and 36b close over base portion 22 and during the latter stages of descent, concrete is pushed sideways only (as shown in FIG. 4B) out of the open ends 40. As piston rods 42 descends, the shape of space enclosing the concrete changes (it is reduced to the space between the shear box 34 and the base portion 22), forcing the concrete out of shear box 34. The multiplicity of pressure sensors 18 (not shown), some of which are in orthogonal planes, monitor the changing stresses as the concrete shears due to the shape change. Pressure sensor 46 and stress sensor 31 monitor the resistance to movement of the piston rod 42.

Figure 4C:
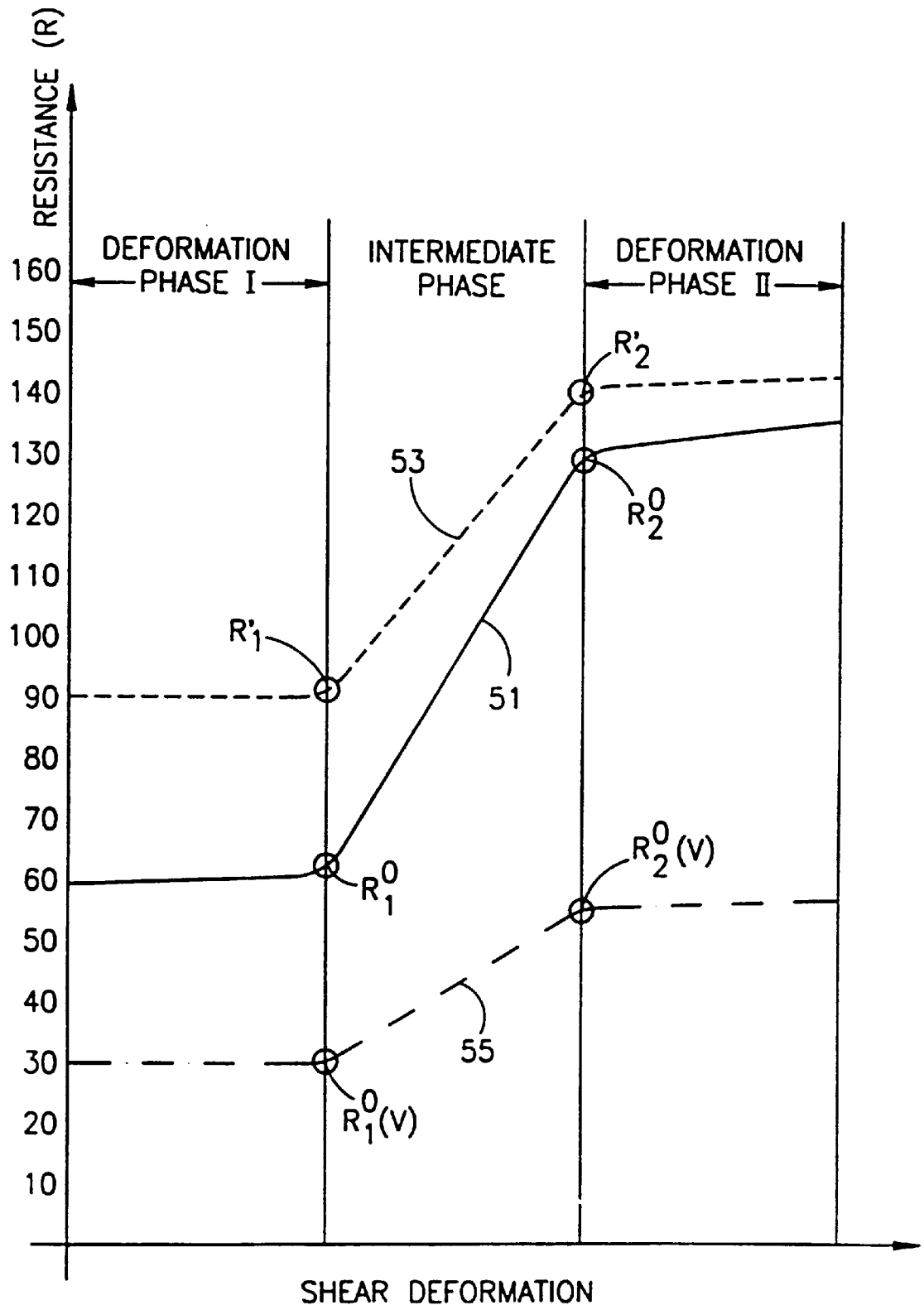
FIG. 4C is a graphical illustration of resistance vs. shear deformation for two mixes deformed with the device of FIG. 2.

FIG. 4C, to which reference is briefly made, illustrates exemplary changes in resistance due to shear deformation for two types of mixes, a first mix, labeled 0, and the first mix with more sand, labeled 1. Resistance measurements are taken as the deformation increases. Curves 51 and 53 show the changing shear resistance for the 0 and 1 mixes, respectively, as the shear box 34 descends. The first datapoint, $R_1^1$ is measured as the shear box 34 begins its descent and the second datapoint $R_2^i$ is measured once the shear box 34 has come to close to its final position. Curves 51 and 53 indicate that a) the resistance is different for the two types of mixes, where the resistance is less in the first mix with less sand, and b) that the resistance changes, by different amounts, as the shear deformation regime changes.

Many different measurements can be taken from the data of FIG. 4C. For example, the sensitivities, $S^0$ and $S^1$, of measurements $R^0$ and $R^1$, respectively, to deformation are defined as:

$$S^0 = \frac{R_2^0 - R_1^0}{R_1^0} \quad (1)$$

$$S^1 = \frac{R_2^1 - R_1^1}{R_1^1}$$

Typically, measurements from all the sensors are gathered over time so that relationships among their outputs can be established. For example, the change in output of the pressure sensor 46 and/or the stress sensor 31 can be examined against readings of sensors 18 or the electric ruler 33.

A third method of operation tests the concrete by measuring the difference in behavior in shear with and without vibration. In this method, frame 14 is subjected to the method described above with and then without vibration. The vibration tends to "liquefy" the concrete and reduce the effect of friction. Optionally, the intensity of the vibration can be controlled, enabling repetition of the operation under a number of vibration levels.

Curve 55 indicates the change resistance for the first mix due to the presence of vibration and should be compared to curve 51. Curve 55 is lower than curve 51, indicating that the resistance to shear deformation is lower in the presence of vibration. In addition, the change in the resistance, from $R_1^0(v)$ to $R_2^0(v)$, over the test is lower in the presence of vibration. The sensitivity $S^0(v)$, otherwise call the "vibratability", is defined as:

$$S^0(v) = \frac{R_1^0 - R_1^0(v)}{R_1^0} \quad (2)$$

Some rheological characteristics of the concrete mass, as manifested during the various testing operations, described hereinabove, can be calculated from the sensor data. For example, the testing machine of FIGS. 2, 3A and 3B can produce some of the following characteristics, defined for the purpose of illustration, any collection of which form a "rheological profile":

a. Workability: A quantitative measure of the resistance to shear deformation of a concrete mass under the influence of an external force. It can be measured with the apparatus of FIG. 2 or by other standard means. For instance, workability can be measured as the resistance to shear at a given rate of deformation or the time it takes to produce a given deformation under a constant force.

b. Stress state sensitivity factor: a coefficient expressing the relationship between the resistance to shear deformation (the workability) of a confined concrete mass and the stress state prevailing in the shear planes;

c. Stress distribution factor: a coefficient expressing the relationship between the level of stresses developing on two orthogonal planes in a concrete mass under the influence of a force vector acting normally to one of the planes;

d. Shear rate sensitivity factor: A coefficient expressing a relationship between the rate of shear induced in a concrete mass and the resulting stresses;

e. Vibration decay factor: A coefficient expressing the rate of change in the intensity of a vibration wave passed through a mass of concrete with respect of change in the distance from the source of the vibration;

f. Vibratability factor: A coefficient expressing the relationship between a change in the intensity of vibration operating on a concrete mass and the change in its resistance to shear deformation in a zone affected by the vibration;

g. Pumpability factor I: A coefficient expressing the relationship between the pumping pressure and the rate of flow of a concrete mass pumped through a pipe;

h. Pumpability factor II: A coefficient expressing the loss of pressure in a concrete mass along its passage through a given route in a piping system;

i. Deformability factor: A coefficient expressing the relationship between the force required to deform a confined mass of concrete and a resulting dimensional change occurring in one of its cross-sections.

It will be appreciated that not all of the characteristics provided hereinabove are required for all mixes. Different combinations of the characteristics, one of which normally is workability, can be utilized, as desired. The parameters forming the rheological profile that are required in a specific situation are determined by the nature of the conditions to which the concrete is to be exposed in the specific application. Furthermore, some of the parameters, such as pumpability, are not measured from the apparatus of FIG. 2 but from the other apparati described hereinbelow.

The data is collected and processed, as will be described hereinbelow. The information can be used, for example, to advise the concrete batching plant of the actual rheology and quality of the concrete. From this information, the mix design changer 6 (FIG. 1) can adjust the concrete mix design to compensate for a change in the constituent characteristics or a change in actual site conditions and thus, allow the plant to produce a more efficient and cost effective mix design.

Creation of Rheological Profile

Reference is now made to FIG. 5 which is a flow chart illustration of the design of a nominal rheological profile. A concrete mix based on a standard mix design having known proportions, for example, a 1:2:4 mix having a water/cement ration of 0.45 is first produced (step 58). A "1:2:4" mix refers to the mix proportions, that is, one part of cement to 2 parts of fine aggregate to 4 parts of coarse aggregate.

A sample of the produced concrete mix is tested (step 60) to determine its properties and to compare it against the desired properties.

A sample of the concrete mix is then placed in a test mold (step 62), to which the concrete testing device 10 is attached. The concrete mix is then subjected to the first of a set of regimes (step 63), which are applicable to the type of concrete mix being tested (step 64), for example constant rate of deformation. The readings from the plurality of sensors are recorded as the concrete undergoes change due to the forces acting on it (step 66). Steps 63 to 66 are repeated for other regimes, such as different rates of deformation with or without vibration. On completion of the applicable tests, the data is processed (step 68). The resulting output defines the nominal rheological profile 70 for the specific mix.

The resultant profile data, together with the mix design proportions and a description of the applications and materials domain under which the mix was produced can be stored in a distance for future access.

Due to the variability of the characteristics of the constituent materials, a mix design with given mix proportions could yield a rheological profile different from the nominal rheological profile that originally corresponded to the mix design, even if the workability values are equal. To achieve a profile which complies with the nominal rheological profile, the present invention adjusts the mix proportions, primarily of the solid elements of the mix, and typically, thereafter, the water and cement contents as well, as will be described hereinbelow. The adjustment is made to control the values of at least two quantitative, measurable parameters of the profile, only one of which defines the resistance to deformation of the concrete mass, namely, its workability. In contrast, prior art methods use trial and error procedures to adjust proportions of water or water and cement so as to produce a mix design with a desired, measurable workability value whilst changes in aggregate constituents aimed to achieve desired characteristics are conducted in a manner based on a concrete technician's subjective assessment.

Overall Method of Controlled Concrete Production

Reference is now made to FIG. 6 which is a flow chart illustrating the use of a nominal rheological profile to adjust the concrete mix proportions. A concrete mix is prepared (step 76) in accordance with a specified design relevant to the type of concrete mix being required. The mix is measured, for example during mixing or pumping, using a selected concrete testing device 10 (step 78) for the specified regime. The recorded measurements are then converted to a rheological profile which reflects the measured mix (step 80). The measured rheological profile is then compared with the designed nominal rheological profile (step 82). If the profile is within predetermined limits, the design is satisfactory (83). If the rheological profile does not comply with the nominal rheological profile (within pre-determined limits), the mix proportions are amended (step 84) in accordance with pre-determined criteria and the revised mix is re-measured (step 78) and steps 80 and 82 are repeated. If the revised mix does not produce the expected rheological profile, steps 84 and 78–82 are repeated until the nominal and measured profiles match.

It will be appreciated that the adjustments to the mix composition can also relate to powdery chemicals which regulate rheological behavior.

For each concrete mix composition there is a matching rheological profile.

Mathematical Description of Mix Adjustment

The concrete mix design can be expressed by a variable p which is a vector of mix proportions, where:

$$p=(p_1, p_2, \ldots, p_k); \quad (3)$$

$$p_1+p_2+ \ldots +p_k=1; \quad (4)$$

k=number of mix components; and $p_i$ is the fraction of component i in the concrete mix. In other words, component i constitutes 100 $p_i$ percent of the mix.

For example, a concrete mix having k=3 components comprising fines (30%), water and cement slurry (42%) and a third component representing all other concrete constituents (28%), may be expressed by:

$$p=(0.3, 0.42, 0.28) \quad (5)$$

The rheological profile is composed of a number (n) of quantitative indices that represent rheological characteristics of the concrete mix, such as workability, stress distribution at a point subjected to an axial load or stress state sensitivity of the shear resistance. The general value of a rheological profile ρ may be denoted by the following vector:

$$\rho=(\rho_1, \rho_2, \ldots \rho_n), \quad (6)$$

where each coordinate $\rho_i$ represents a different rheological characteristic of the mix.

The target or nominal values of a rheological profile ρ* is denoted by:

$$\rho^*=(\rho_1^*, \rho_2^*, \ldots \rho_n^*). \quad (7)$$

The aim is to find a value for the independent variable p (mix proportions) which will yield a value ρ for the dependent rheological profile variable which is "adequately close", that is, within pre-determined limits, of the nominal value ρ*. The phrase "adequately close" differentiates between constrained rheological characteristics $\rho_i$ that satisfy the condition of:

$$\rho_1 \leq \rho_1^*, \rho_2 \leq \rho_2^*, ,\rho_b \leq \rho_b^*; \text{ and} \quad (8)$$

target characteristics that must be fitted as close as possible to their corresponding nominal values:

$$\rho_{b+1} \approx \rho^*_{b+1}, \rho_{b+2} \approx \rho^*_{b+2}, , \rho_n \approx \rho^*_n; \quad (9)$$

The phrase "adequately close" can be typically defined as:

$$A_{b+1}(\rho_{b+1}-\rho^*_{b+1})^2+ \ldots +A_n(\rho_n-\rho^*_n)^2 \leq D; \quad (10)$$

where: $A_{b+1}, \ldots, A_n$ are positive numbers modeling the severity of errors and D is a positive number modeling the tolerance allowed in the global departure from the nominal values.

It is assumed that the rheological profile is a function of the concrete mix proportions as long as the same materials are used. If the constituent materials change, so does this function. This is the main reason for the need to re-calibrate the mix proportions so as to achieve the nominal value of the rheological profile of the original mix.

The Search Process

To determine the mix proportions required for a mix having a given rheological profile, several concrete mixes, each having different mix proportions, are produced. The specific rheological characteristics and hence, the rheological profile of each mix, are calculated. Since each concrete mix has different proportions, each of the rheological characteristics may have different values. Using standard mathematical tools, such as the method of least squares, splines or interpolation polynominals, applied iteratively, a "best-fit" curve, covering the range of values for each rheological characteristic, can be obtained.

The formula for the determination of the initial steps in the search process could be mathematically calibrated using training data from laboratory experiments on the materials or based on arbitrary field practice or general assessment.

With the assistance of suitable calculating tools, that are part of computer software programs commercially available, such as the Excel Spreadsheet produced by Microsoft Corporation of the USA, any mix composition can be simulated under the best-fit curve. A mix composition yielding the desired nominal rheological profile under the best-fit model can be calculated and produced.

The rheological characteristics of the actual mix are compared with the characteristics of the design and if the rheological profiles do not match, the model is amended following the introduction of the new sample point. The mix proportions are amended accordingly (step 84 of FIG. 6). The incremental changes in the mix proportions are mathematically designed so as to achieve the desired new mix design.

Thus, it is possible to design a concrete mix which matches some required properties of the mix made with the original material. This allows for a better control over the production of concrete mixes. Steps 80–84 are repeated until the rheological profile of the produced mix matches the pre-determined criteria for that mix.

This mathematical simulation procedure can find a domain of feasible approximate solutions, (that is, the mix compositions are feasible with respect to the interpolation function). The choice of mix is made taking account of economic considerations, that is, the cost optimization function sets boundaries in the search procedure.

Standard analysis software packages, such as the EXCEL spread sheet by Microsoft Corp. of the USA, or more advanced mathematical programs such as the Mathematical from Wolfram Research Inc. of Champagne Ill., U.S.A. or MATLAB manufactured by The Math Works Inc. of the USA, contain tools for the minimization of linear or non linear objective functions subject to a set of constraints, which can be incorporated within the mathematical formula for the calculation of the economically efficient mix compositions. These mathematical techniques will be applied in the context of the invention not only to the objective defined above, namely, the search for a concrete mix composition that matches adequately close a given target rheological profile, but also to situations where such a nominal profile is fully or partially absent. In this case, the same interpolation and search procedure will be applied to find a concrete mix composition that optimizes a given criterion function. For example, it may be applied to:

a. minimize the cost of the concrete mix whilst maintaining the pressure on the piston of a pump as required to push concrete at a given rate through a given pipe system;

b. minimize the cost of the concrete mix whilst maximizing the bulk density of a concrete block produced under a given regime, c. minimize water/cement ratio of a block making mix maximizing the compressive strength of a freshly made block (prior to hardening); or d. minimize the cost of a concrete mix whilst maintaining force required to rotate the drum of a concrete mixer at a given rate under given conditions.

Controlling Concrete Production Under Other Conditions

Figure 7:
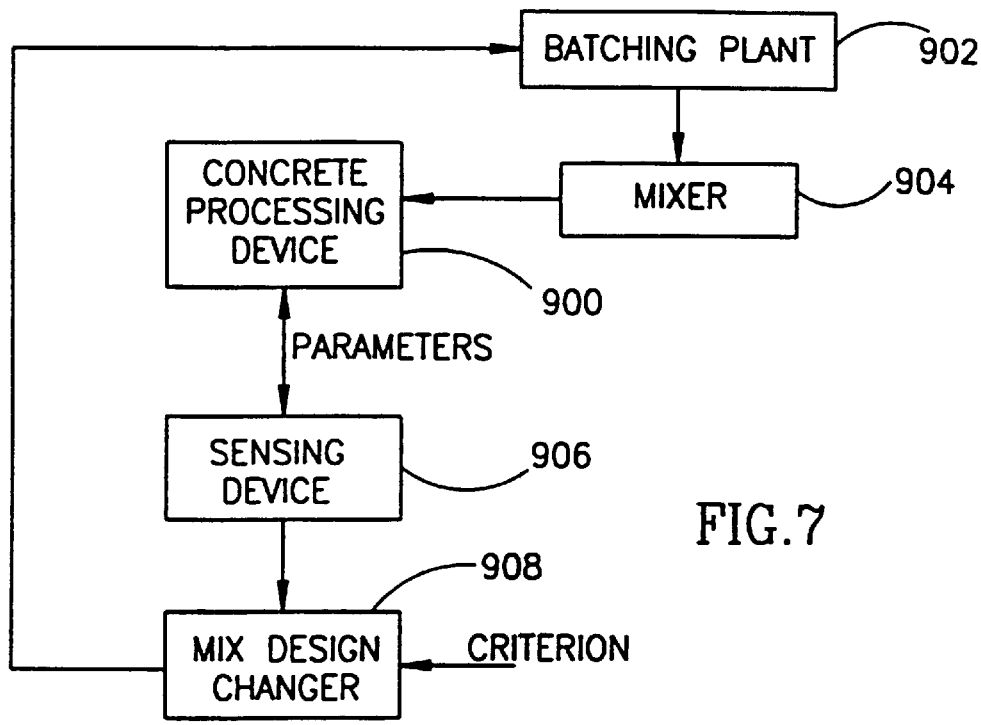
FIG. 7 is a block diagram illustration of an application of the invention in a alternative, optimizing mode.
Figure 8:
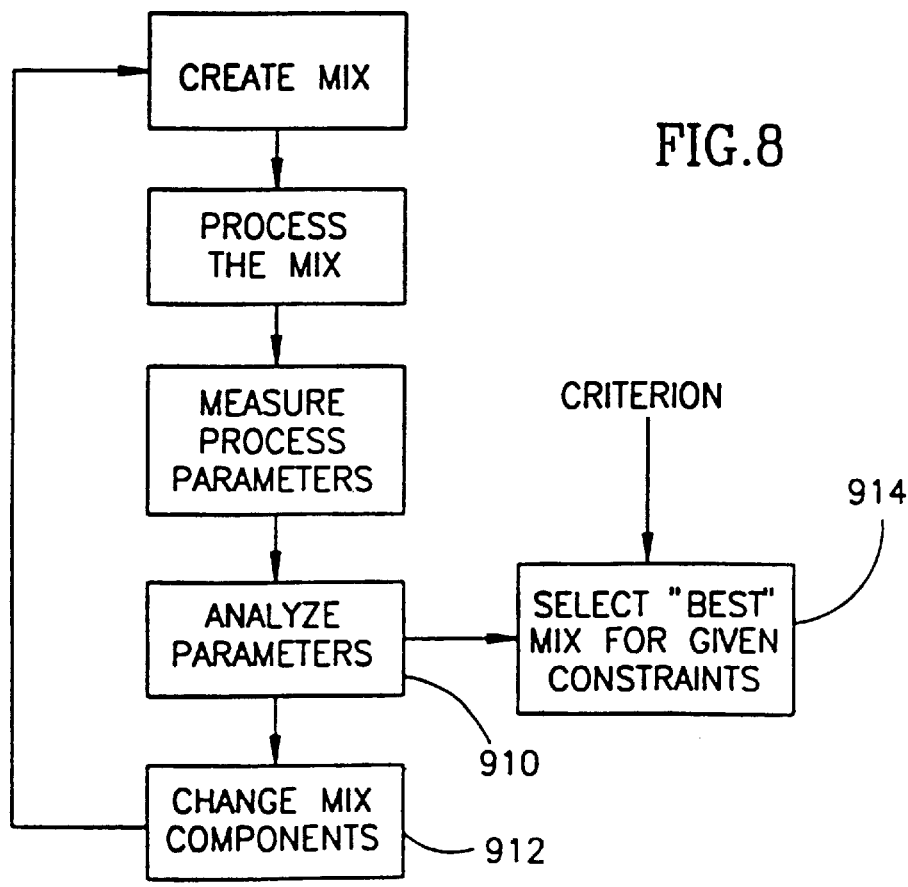
FIG. 8 is a flow chart illustration of the operation of the system of FIG. 7.

The alternative method is operative with a concrete processing device, such as a pump or a block making machine, as illustrated in the flow chart of FIG. 7, to which reference is made. Reference is also made to FIG. 8 which illustrates, in flow chart format, the alternative method.

The concrete processing device, labeled 900, receives already mixed concrete from a batching plant 902 via a mixer 904. A sensing device 906, which can have more than one sensor therein, monitors various parameters of the operation of the processing device 900. For example, if the processing device 900 is a piston pump which forces concrete through a pipe system, the sensing device 906 monitors the force or pressure on the pump, the extension of the piston and the rate at which concrete exits the pipe system. No measurements of the concrete itself are taken.

The output of the sensing device 906 is provided to a mix design changer 908 which, as indicated in step 910 of FIG. 8, analyzes the parameters and, in step 912, provides change commands to the batching plant 902 to change the amount of fine sand (or other solid components of the mix). The process is repeated a number of times.

In step 914, the mix design changer 908 reviews the design mix at each point and its resultant parameter and selects the design mix which provides a desired set of parameter values within a given constraint. For example, it might select the lowest cost mix design which provides concrete that flows in the given pump at a rate of 2 meter/sec and utilizes the maximum amount of force at which the pump can operate.

Alternative Embodiments of the Concrete Tester

Figure 9A:
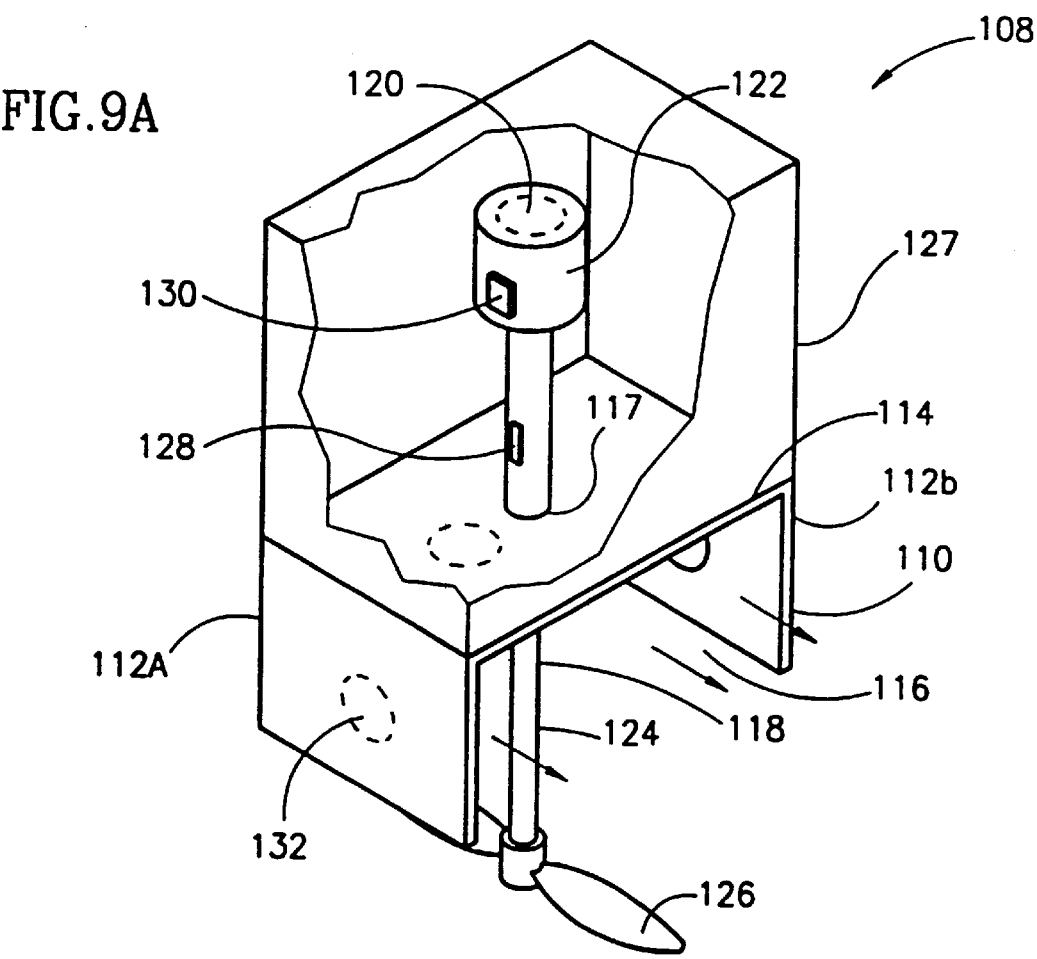
FIG. 9A is an isometric illustration of a concrete testing device in accordance with a second preferred embodiment of the present invention.
Figure 9B:
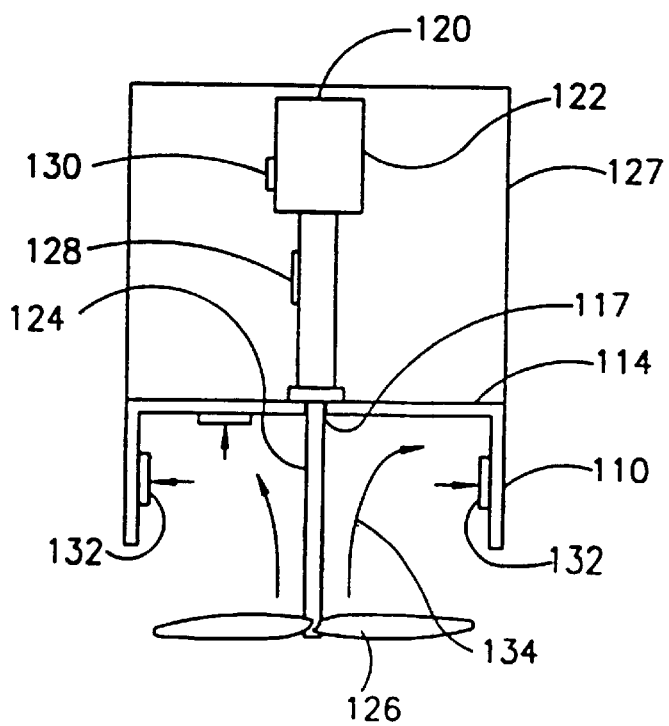
FIG. 9B is a sectional elevation of the concrete testing device of FIG. 9A.

Reference is now made to FIGS. 9A and 9B which illustrate a second embodiment of the concrete testing device, generally designated 108. The testing device 108 comprises a shear box 110 and a propeller 118. Shear box 110 comprises two side panels 112a and 112b connected to a base panel 114 and has open sides 116. An aperture 117 is formed within base panel 114 for the insertion of propeller 118.

Propeller 118 comprises an electrical motor 120 enclosed within a housing 122. A vertical drive shaft 124, suitably retained by housing 122, is attached to propeller blades 126. Drive shaft 124 and propeller blades 126 extend below shear box 110 and are retained in position by any suitable means which allows drive shaft 124 to freely rotate. Housing 122 and motor 120 are enclosed within a chamber 127 to protect them from the concrete. A tachometer 128 is connected to shaft 124 to measure the speed of rotation of propeller 118. An ammeter 130, or similar electrical measuring device, is fitted to the upper part of housing 120 to measure the power used by propeller 118. Furthermore, changes in current occurring within each cycle in the propeller rotation are also recorded.

A multiplicity of stress sensors 132 are fitted to the underside of side panels 112a and 112b and base panel 114 of shear box 110. As described hereinabove with respect to the embodiment of FIG. 2, the sensors are in two planes so that the stress state in the concrete can be monitored.

In operation, shear box 110 is inserted into the concrete mass, and propeller mixer 118 is switched on. Propeller blades 126 rotate, forcing the concrete forward (indicated by arrows 134 in FIG. 9B) and causing the concrete to shear. When the propeller blades rotates, they are below the side planes 112a and 112b half of the time and away from them the other half of the time. Thus, the shape of space within which the concrete is held changes cyclically. For various speeds of propeller 118, the current, mixer speed and sensor data are collected and passed on to the processing unit (not shown), as hereinabove described.

Figure 9C:
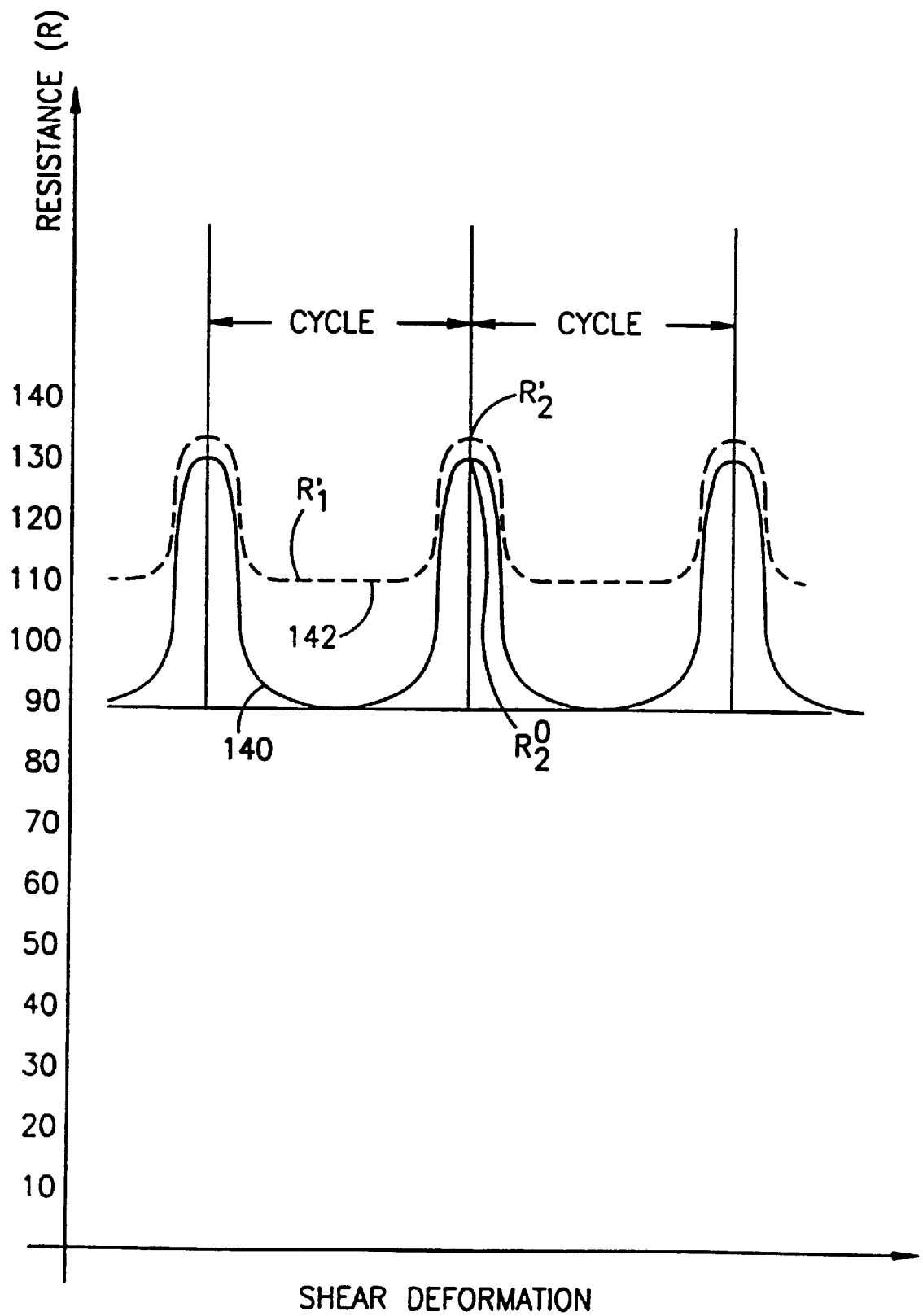
FIG. 9C is a graphical illustration of resistance vs. shear deformation for two mixes deformed with the device of FIGS. 9A and 9B.

FIG. 9C, to which reference is now briefly made, illustrates exemplary resistance vs. shear deformation results for the two mixes of FIG. 4C within the embodiment of FIGS. 9A and 9B. Since the shape of the space within which the concrete is held changes cyclically, the curves of FIG. 5C, labeled 140 and 142, change periodically. The resistance datapoints of interest are those at the extreme ends of one cycle of change. Thus, the two datapoints $R_1^0$ and $R_2^0$ of the first mix are spread further apart than are the two datapoints $R_1^1$ and $R_2^1$ of the second mix.

Figure 10A:
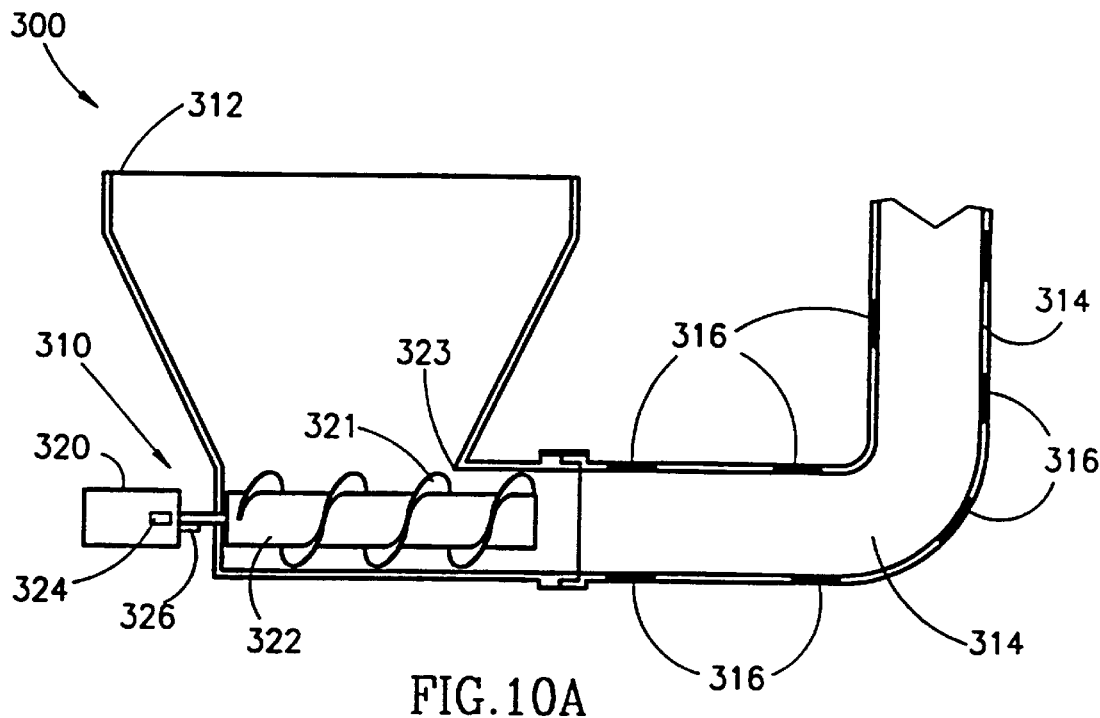
FIG. 10A is a sectional elevation of a concrete testing device in accordance with a fourth preferred embodiment of the present invention.
Figure 10B:
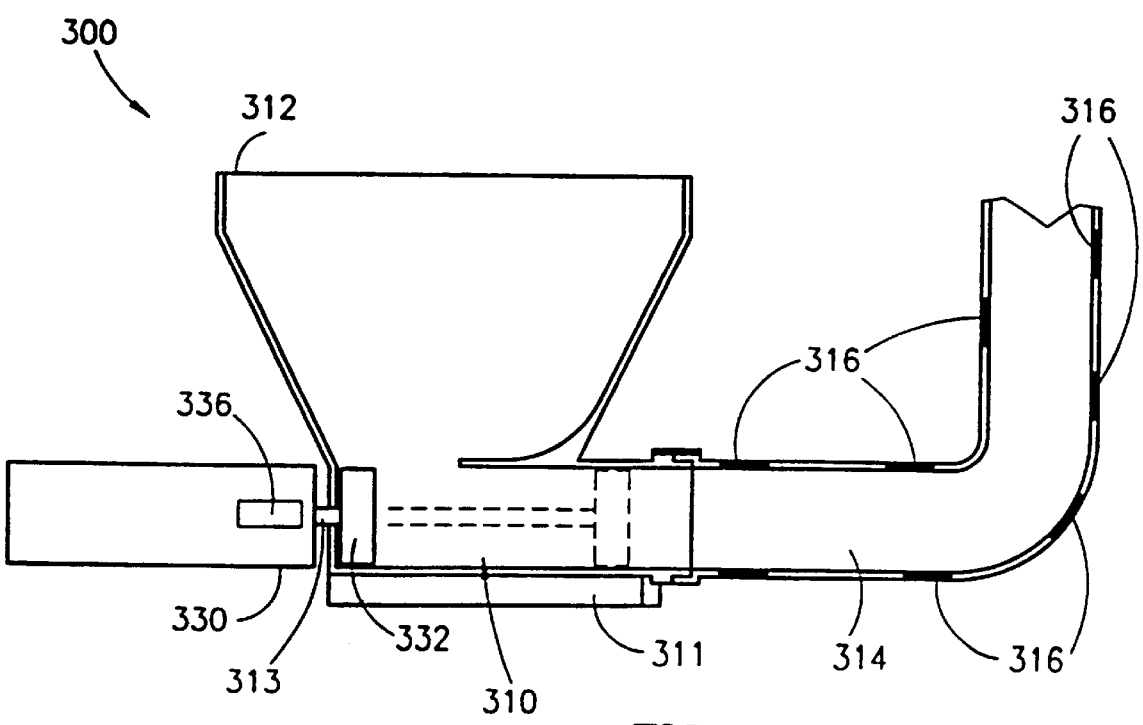
FIG. 10B is a sectional elevation of a concrete testing device in accordance with a fifth preferred embodiment of the present invention.

Reference is now made to FIGS. 10A and 10B which illustrate a device for testing concrete within a pumping system, generally designated 300, constructed and operative in accordance with a fourth and fifth embodiment of the invention. This embodiment measures at least the pumpability factors I and II and the shear rate sensitivity factor, as described hereinabove.

Generally, concrete pumping system 300 comprises a pump 310 and a hopper attachment 312 coupled to a system of pipes 314. A multiplicity of pressure sensors 316 are attached to the inside of pipes 314. Sensors 316 sense the changing pressure and stress levels as the concrete is pumped through the pipes 314. Additionally various sensing devices, described in detail hereinbelow, are connected to pump 310 to measure operational parameters of the pump.

In operation, concrete is discharged into hopper 312 and forced along the system of pipes 314 by the action of the pump 310, where the pump cyclically changes the shape of the space through which the concrete is pumped. As hereinabove described with respect to FIG. 2, the data is collected and passed onto the processing unit 100 for processing. Means, as known in the act, are provided to prevent backflow from pipe 314 into the pump.

In the concrete pumping system illustrated in FIG. 10A, an electric pump 320 is attached to a screw device 322 which propels the concrete along pipes 314. The sensing devices also comprises an ammeter 324, or other similar measuring device, which is fitted to pump 310 to measure the current used by electric pump 310 whilst changes in current occurring within each cycle of the screw rotation or position movement are also recorded. A tachometer 326, or other similar device for measuring the speed of rotation of screw device 322, is fitted to pump 320. It is noted that, as the screw 322 rotates, the distance between the upper part of the screw, labeled 321, and the pipe entrance, labeled 323, changes cyclically.

In the concrete pumping system 300 illustrated in FIG. 10B, a hydraulic pump 330 is attached to a piston device 332, such as a single piston or double piston action, as is known in the art. The action of the piston propels the concrete along pipes 314, slowly changing the shape of the space through which the concrete is pumped. In this embodiment, the sensing devices comprise a manometer 336, or similar device, for measuring the hydraulic pressure of the hydraulic pump 330. In addition, the system of FIG. 10B has an electronic ruler 313 to measure the displacement of the pump. This embodiment can also include a vibrator 311 to provide a measurement of vibratability.

Figure 11:
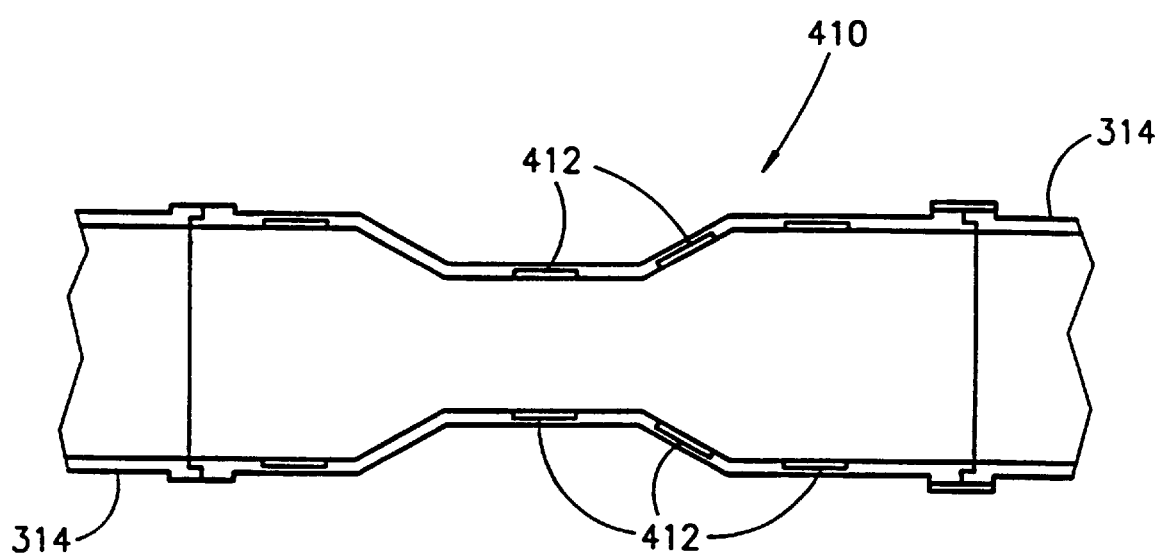
FIG. 11 is a sectional elevation of specially adapted pipes used with a concrete testing device in accordance with one of the preferred embodiments of the present invention.

Reference is now briefly made to FIG. 11 which illustrates the use of specially adapted pipe inserts within the pumping system 300, for testing the concrete. Similar elements in FIG. 11 serve similar functions and are referenced by similar reference numerals.

In FIG. 11, an adapted pipe 410, having a generally smaller diameter than the standard pipes 314 of pumping system 300, described above, is coupled to the pipes 314. A multiplicity of pressure sensors 412 are attached to the inside of adapted pipe 410. The changing stress state of the concrete due to the change in shape of the pipe can be monitored from the data supplied through the multiplicity of sensors 412 fitted within adapted pipe 410 and standard pipes 314, both upstream and downstream of adapted pipe 410.

Figure 12:
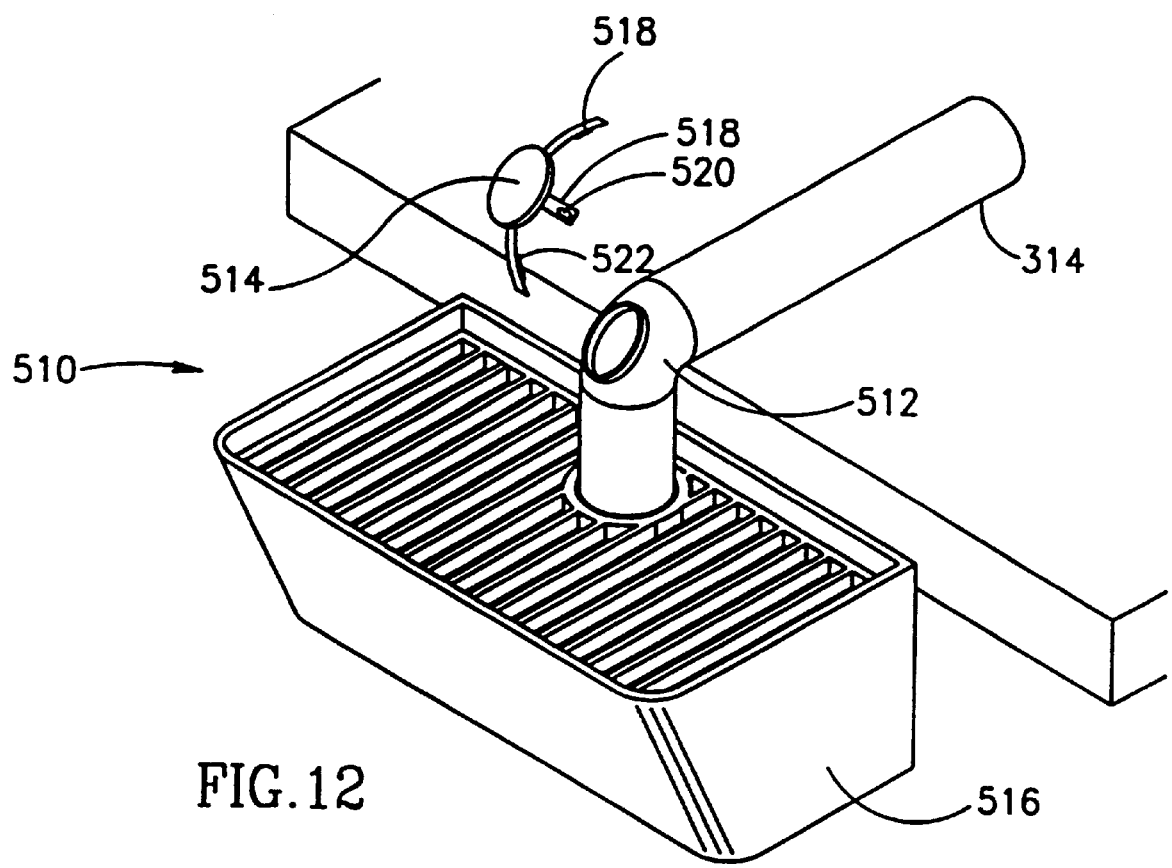
FIG. 12 is an isomeric view of a concrete testing device in accordance with a sixth preferred embodiment of the present invention.
Figure 13:
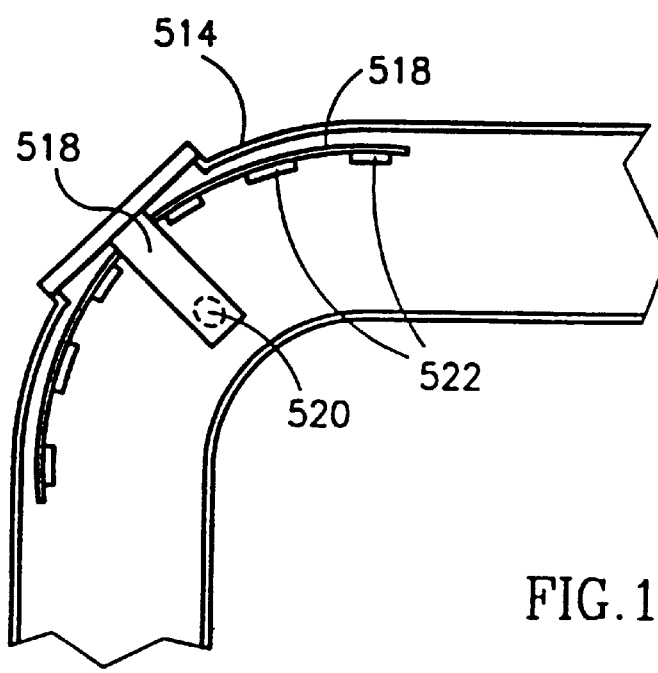
FIG. 13 is a sectional detail of the concrete testing device adapted to be inserted into a 90 degree pipe bend of a pumping system described in FIG. 12.

Reference is now briefly made to FIGS. 12 to 13. FIG. 12 illustrates an isometric view of a sixth embodiment of the concrete testing device, generally designated 510. FIG. 13 shows a sectional detail of concrete testing device 510 which is specially adapted to be inserted into a 90 degree pipe bend 512 of a pumping system.

A 90 degree bend 512 is generally used, for example, in a pumping system where the concrete is pumped upwards out of hopper 516 (as illustrated). The device 510 measures the changing stress state and loss of pressure caused by sharp bends.

Testing device 510 comprises a locking cover plate 514, which replaces a cover plate, commonly fitted at the exit (or entrance) of a pipe system. Flexible strips 518 extend perpendicularly from the inside face of cover plate 514. Sensors 520 and 522 are fitted to flexible strips 518.

Figure 14A:
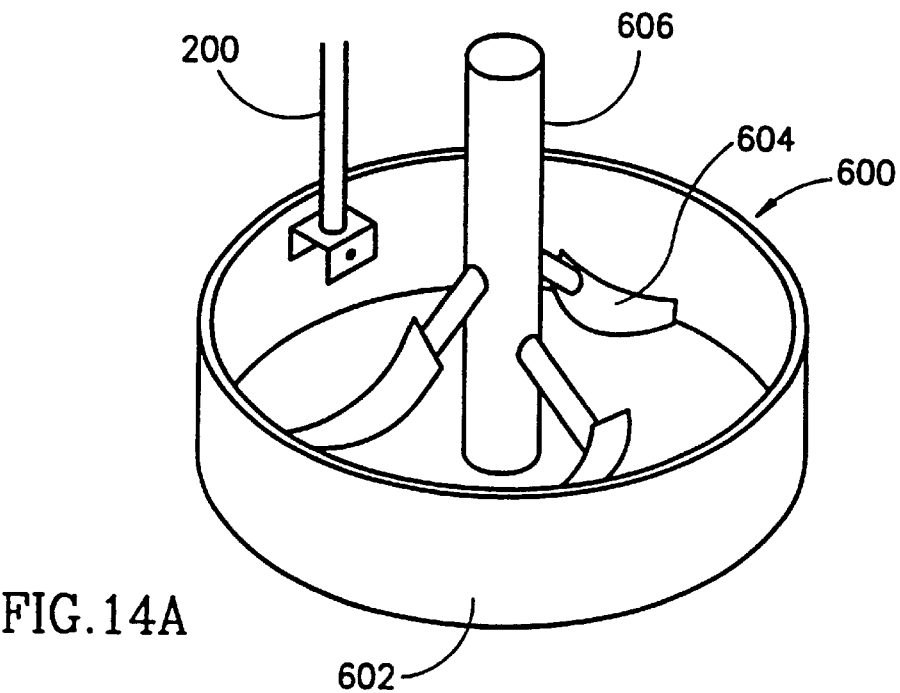
FIG. 14A is an illustration of the use of a concrete testing device as in FIG. 2 or FIG. 9 with a paddle mixer.
Figure 14B:
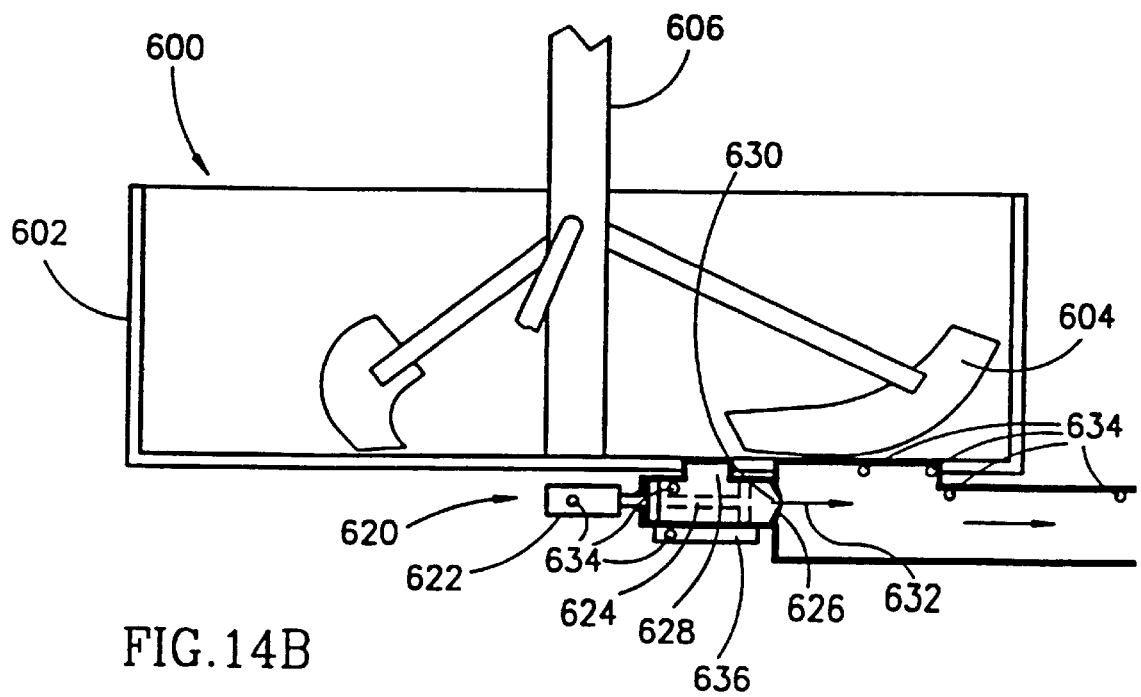
FIG. 14B is an illustration of the use of a concrete testing device in accordance with a seventh preferred embodiment of the present invention.

Reference is now made to FIGS. 14A and 14B which illustrate the use of a concrete testing device with a paddle mixer, generally designated 600. Concrete testing device can be any concrete testing devices, constructed in accordance with the preferred embodiment of the present invention. FIG. 14A illustrates a concrete testing device 200, described hereinabove with respect to FIG. 10, which can be inserted into paddle mixer 600 from above when the paddle mixer is stationary. FIG. 14B illustrates a concrete testing device, generally designated 620, located below paddle mixer 600.

Generally, concrete paddle mixer 600 is a standard paddle mixer, known in the art, which comprises a mixing pan 602, and a plurality of paddles 604 attached to a revolving shaft 606. To mix the concrete, shaft 606 cause paddles 604 to revolve. The mixing action forces the concrete out of the bottom of pan 602. Data is collected by concrete testing device 200 and passed on to the processing unit (not shown), as previously described.

Referring now to FIG. 14B, concrete testing device 620, comprises a hydraulic pump 622 attached to a piston device 624, such as a single piston or double piston action, as is known in the art. Piston device 624 is enclosed within a housing 626, located beneath pan 602, having an inlet gate 628 and an outlet 630 constructed therein. An opening 632 is constructed in the base of pan 602 to accommodate inlet gate 628. A multiplicity of sensors 634 are attached to piston device 624, such as to measure the pumping pressure, displacement of the piston and the stress state along the pipe. Optionally, a vibrator 636 can be fitted to the base of piston device 624.

When inlet gate 628 is opened and concrete enters housing 626, the action of piston device 624 pushes the concrete through opening 632. Measurements can be made with or without vibration as desired. Data is collected by the multiplicity of sensors 634 and passed on to the processing unit (not shown), as previously described.

Figure 15:
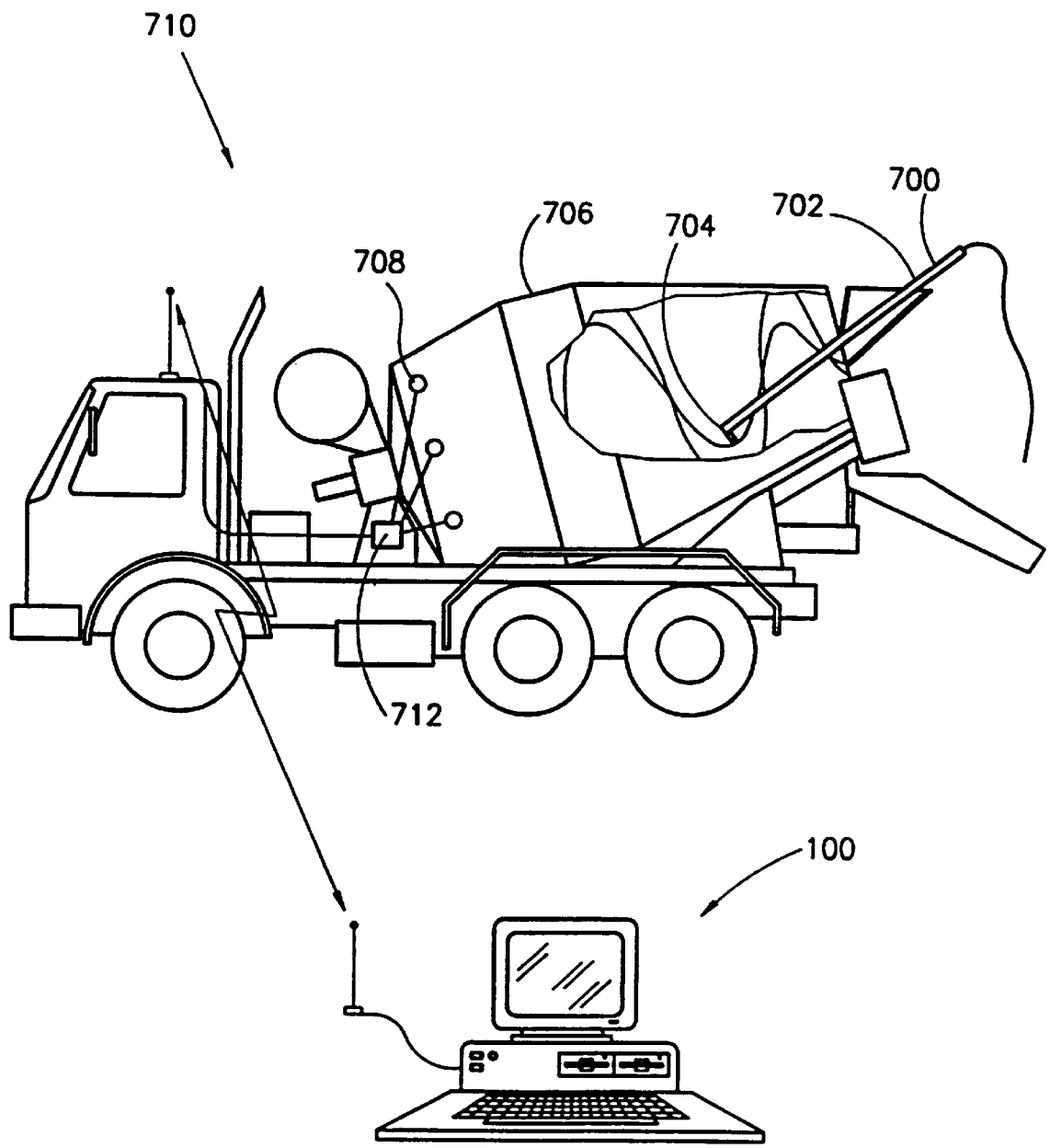
FIG. 15 is an illustration of the use of the concrete testing device adapted for use with a mobile mixer.

Reference is now made to FIG. 15, which illustrates a concrete testing device 700 adapted for use with a mobile mixer 710. Concrete testing device 700 comprises a rod 702 having a plurality of sensors 704 attached to one end thereof. In one mode of this embodiment, the deformation is provided by the rotating drum 706. Alternatively, the rod can include a mechanical deforming unit with monitoring sensors, such as shown in FIG. 9. Rod 702 is inserted within the drum 706 of mixer 710. Data collected by sensors 704 are passed on to the processing unit 100, as previously described. Optionally, a multiplicity of sensors 708 can be attached to a shear box mounted on the inside of drum 706. In such a device, the output of the sensors is provided to a processing unit 712 located on the rotating drum which transmits the data, typically in a wireless fashion, to remotely contact processing unit 100, which may, for example, be situated at the mixing plant.

Figure 16:
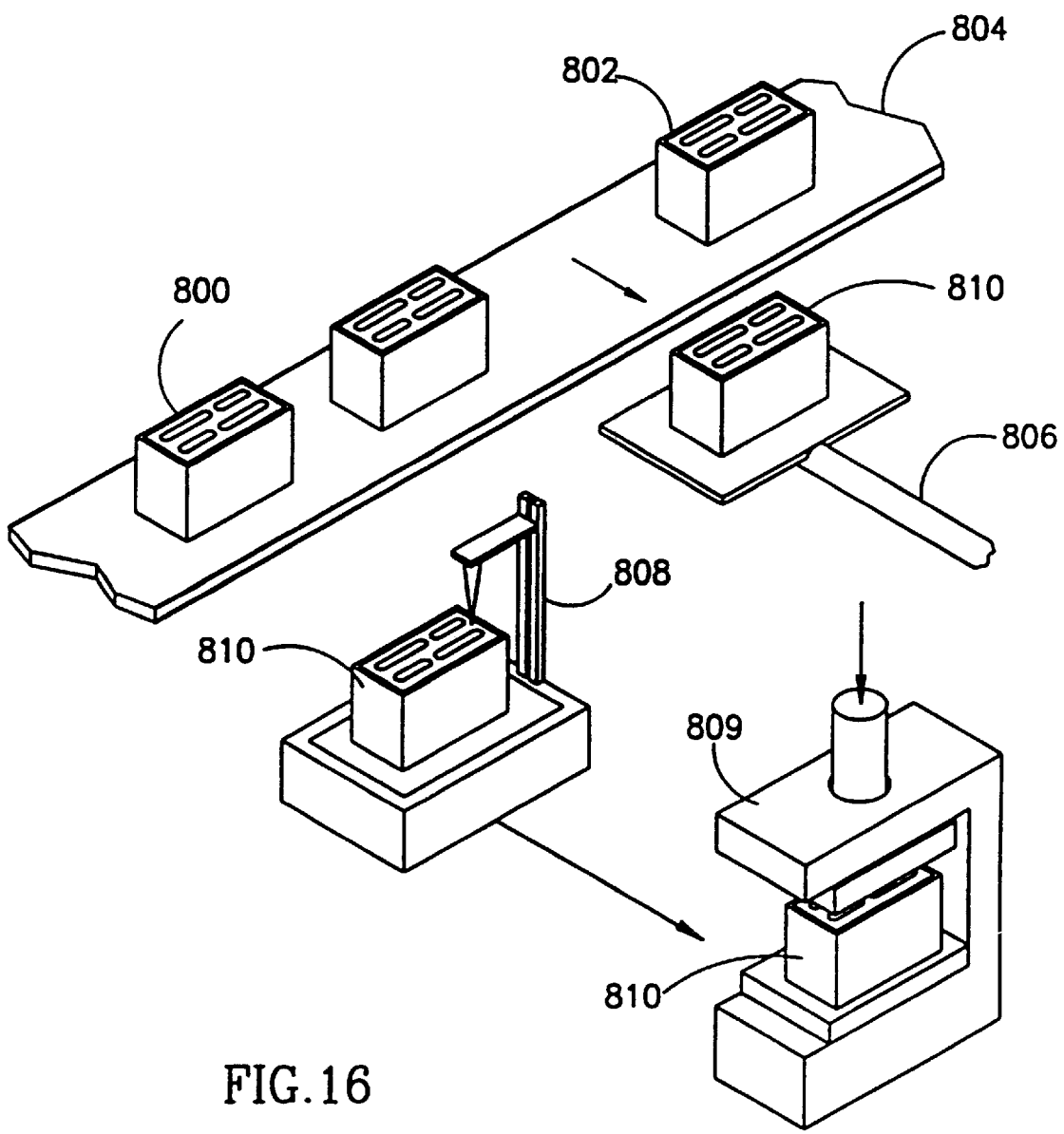
FIG. 16 is an illustration the production control of concrete blocks in accordance with an eighth preferred embodiment of the present invention.

Reference is now made to FIG. 16, which illustrates the production control of concrete blocks 800, of a type commonly manufactured for use in the construction industry, wherein concrete is cast in a mould 802 defining the shape of the concrete block 800. A factory production line 804 is shown on which a plurality of cast concrete blocks 800 are placed. In order to control the production quality and cost, one of the plurality of concrete blocks 800, designated 810, is removed from the production line 804 for testing. The weight and size of the concrete block 810 can be measured using electronic measuring devices 806 and 808, respectively, known in the art. A compression testing frame 809 measures the fresh compressive strength of the block 810. If desired, the rheological profile of the mix used for creating the blocks can be determined using a selected concrete profile measuring device 10, as hereinbefore described. In this case, the rheological profile of the fresh mix is gained with the measurements of the block and compared with the nominal rheological profile for this type of block, and if it does not match, the mix proportions can be adjusted as hereinbefore described with respect to FIG. 6. Alternatively, only the block measurements can be produced and an optimization such as described in FIGS. 7 and 8 can be preformed.

As will be appreciated by persons knowledgeable in the art, the various embodiments hereinabove referred are given by way of example only and do not in any way limit the present invention. For example, apart from the illustrated changes of fines, water and cement, the addition of chemical additives can be controlled to provide a desired rheology.

Those skilled in the art will be readily appreciate that various changes, modifications and variations may be applied to the preferred embodiments without departing from the scope of the invention as defined in and by the appended claims.

What is claimed is:

1. A measuring system for measuring rheological properties of a concrete mix tested when contained, the system comprising:

a shearing unit having a shearing unit contact surface for effecting shear deformation in a volume of said mix; and at least one sensor which senses a measure of a force which is transferred to said concrete mix as a result of said shear deformation under at least two measurement environments, said environments defining at least two different stress states, wherein said two measurement environments are created by said shearing unit and wherein said two different measurement environments have substantially different levels of stresses acting in a direction perpendicular to shear planes formed in said mix by said shear deformation.

2. A measuring system according to claim 1 and additionally comprising a vibrator.

3. A measuring system according to claim 1 and additionally comprising a processor which receives measurements from said at least one sensor and generates, from the measurements relating to said at least two measurement environments, at least one variable relating to the workability of said concrete mix and at least one additional variable produced from the ratio of two of said at least two measurements.

4. A measuring system according to claim 1 and wherein said shearing unit is any one or a combination of the following means: a mechanical mixer, a paddle mixer, a mechanical screw, a plunger, a hydraulic pump, a propeller and a rotatable drum.

5. A measuring system according to claim 1 and wherein said at least one sensor is any one or a combination of the following sensors: an accelerometer, a pressure transducer, a load transducer and an electronic ruler.

6. A measuring system according to claim 1 and wherein said at least one sensor is mounted on said surface and senses a measure of a force vector in a direction generally normal to shearing planes within a measurement environment of said at least one sensor.

7. A measuring system according to claim 1 and wherein said at least one sensor is at least two sensors located on two non-parallel planes of said surface.

8. A measuring system according to claim 1 and wherein said at least one sensor is at least two sensors located in two different measurement environments along said surface.

9. A system according to claim 1, comprising a surface in contact with part of said mix.

10. A system according to claim 1, wherein at least a first sensor of said at least one sensor is mounted on said shearing unit.

11. A method for generating a rheological profile of a given concrete mix, the method comprising:

effecting shear deformation in a mass of said concrete mix;

sensing at least two measures of at least one physical parameter relating to the resistance of said concrete mass to said shear deformation;

generating from at least one of said at least two measures, at least one variable relating to the workability of said concrete mix;

generating at least one additional variable from a mathematical function of at least two of said at least two measures; and creating said rheological profile from said variables.

12. A method according to claim 11, wherein said two measures are determined in two measurement environments which are characterized by having substantially different levels of stresses acting in a direction perpendicular to shear planes formed in said mass by said shear deformation.

13. A method according to claim 12 and wherein sensing occurs simultaneously at at least two different location points in the concrete mass.

14. A method according to claim 12 and wherein sensing occurs at a single location in said concrete mass under at least two deformational regimes.

15. A method according to claim 12 and wherein sensing occurs at least once while said mass is under vibration.

16. A method according to claim 12 and wherein said measure of said force is any of the following variables; velocity, voltage, flow rate, acceleration, pressure and force.

17. A method according to claim 12 and wherein sensing senses a measure of a force vector normal to shearing planes within a measurement environment of a sensor.

18. A measuring system according to claim 4 and wherein said surface is an element of any one or a combination of the following containers: a pipe, a box, a drum, a block forming frame and an element of a surface of said shearing unit.

19. A method for the control of production and the design and adjustment of concrete mixes to have desired rheological properties, the method comprising:

preparing a concrete mix in a concrete plant in accordance with a mix design indicating the proportions of solid components and water content of the concrete;

testing said prepared concrete mix with a concrete tester;

generating a rheological profile of said concrete mix from output of said step of testing;

comparing said generated rheological profile with a desired rheological profile defining desired properties of the concrete to be produced by said plant; and adjusting said proportions of said solid components of said mix design in order to produce concrete having a rheological profile which is compatible with said desired rheological profile.

20. A method according to claim 19 and wherein preparing, testing and generating are repeated for at least three concrete mixes, at least two of which have different proportions of solid components and at least two of which have different water to solid ratios.

21. A method according to claim 19 and wherein said desired rheological profile comprises a set of rheological properties each of which has a range of allowable values.

22. A method according to claim 19, wherein testing is conducted while at least part of the concrete mix flows through a testing apparatus.

23. A method according to claim 19, wherein said rheological profile comprises:

at least one measure of the resistance to deformation of a mix under a given deformation; and at least one quantitative indicator of a sensitivity of the resistance to deformation of said mix to stresses acting in said mix in a direction perpendicular to shear planes formed in said mix under a deformation.

24. A system which designs, adjusts and produces concrete to have desired rheological properties during times of concrete preparation and production, the system comprising:

a plant for preparing a concrete mix in accordance with a mix design indicating the proportions of the solid components and water of the concrete;

a concrete profile measuring unit for measuring a rheological profile of the concrete produced by said plant; and a mix changing unit for receiving said measured rheological profile and a desired rheological profile "defining desired properties of the concrete produced by said plant", and for indicating to said plant to adjust said solid components of said concrete mix, as many times as necessary, in order to produce concrete which has a rheological profile which is compatible with said desired rheological profile.

25. A system according to claim 24 and wherein said mix changing unit comprises a search unit for receiving a quality of change criterion and for determining the mix design change which will provide concrete having said rheological profile which is compatible with said desired rheological profile and which fits within said quality of change criterion.

26. A system according to claim 24 and wherein said concrete profile measuring unit is located away from said plant.

27. A system according to claim 24 and wherein said concrete profile measuring unit is located within said plant.

28. A system according to claim 24 and wherein said concrete profile measuring unit comprises a measuring system for measuring rheological properties of a concrete mix tested when contained, the system comprising:

a surface in contact with a part of a mass of said concrete mix;

a shearing unit for effecting shear deformation in said mass; and at least one sensor which senses a measure of a force which is transferred to said surface by said concrete mass as a result of said shear deformation under at least two measurement environments defining at least two different stress states.

29. A system according to claim 24 wherein said rheological profile comprises:

at least one measure of the resistance to deformation of a mix under a given deformation; and at least one quantitative indicator of a sensitivity of the resistance to deformation of said mix to stresses acting in said mix in a direction perpendicular to shear planes formed in said mix under a deformation.

30. A system according to claim 28, wherein said two stress states are characterized by having substantially different levels of stresses acting in a direction perpendicular to shear planes formed in said mass by said shear deformation.

31. A method of establishing a rheological profile characterizing a resistance to an applied deformation of concrete mixes comprising:

applying a shear deformation to a mix having a certain composition;

establishing at least one measure of the resistance to deformation of said mix under a given deformation;

establishing at least one quantitative indicator of a sensitivity of the resistance to deformation of said mix to stresses acting in said mix in a direction perpendicular to shear planes formed in said mix under said deformation; and associating said at least one measure of the resistance and said at least one quantitative indicator of a sensitivity to provide a rheological profile of said mix.

* * * * *